United States Patent

Saccomano et al.

[11] Patent Number: 5,414,127
[45] Date of Patent: May 9, 1995

[54] CALCIUM INDEPENDENT CAMP PHOSPHODIESTERASE INHIBITOR ANTIDEPRESSANT

[75] Inventors: Nicholas A. Saccomano, Ledyard; Fredric J. Vinick, Waterford, both of Conn.

[73] Assignee: Pfizer Inc., New York, N.Y.

[21] Appl. No.: 184,092

[22] Filed: Jan. 19, 1994

Related U.S. Application Data

[62] Division of Ser. No. 984,190, Nov. 20, 1992, Pat. No. 5,294,730, which is a division of Ser. No. 854,136, Mar. 19, 1992, Pat. No. 5,196,426, which is a division of Ser. No. 696,690, May 30, 1991, Pat. No. 5,128,358, which is a division of Ser. No. 155,932, Jan. 19, 1988.

[51] Int. Cl.⁶ ............... C07C 211/27; C07C 223/02; C07C 225/18
[52] U.S. Cl. ........................... 564/344; 564/372
[58] Field of Search ..................... 564/344, 372

[56] References Cited

U.S. PATENT DOCUMENTS

| | | | |
|---|---|---|---|
| 3,636,039 | 1/1972 | Gruenman et al. | 260/309.7 |
| 3,772,288 | 11/1973 | Hardtmann et al. | 260/251 R |
| 3,923,833 | 12/1975 | Gruenman et al. | 260/340 |
| 4,006,243 | 2/1977 | Strehlke et al. | 424/273 |
| 4,012,495 | 3/1977 | Schmiechen et al. | 424/274 |
| 4,153,713 | 5/1979 | Huth et al. | 544/142 |
| 4,193,926 | 3/1980 | Schmiechen et al. | 544/141 X |
| 4,261,995 | 4/1981 | Weinhardt et al. | 544/330 X |
| 4,308,278 | 12/1981 | Schneider et al. | 548/317 X |
| 4,322,421 | 3/1982 | Weinhardt et al. | 424/251 |
| 4,567,267 | 1/1986 | Wei et al. | 546/114 |
| 4,582,834 | 4/1986 | Stenzel | 514/274 |

FOREIGN PATENT DOCUMENTS

| | | |
|---|---|---|
| 1451154 | 7/1966 | |
| 1588639 | 4/1981 | United Kingdom . |

Primary Examiner—Jospeh Paul Brust
Attorney, Agent, or Firm—Peter C. Richardson; Gregg C. Benson; Mervin E. Brokke

[57] ABSTRACT

Antidepressant agents having the formula

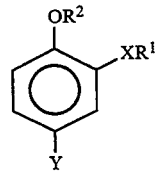

wherein $R^1$ is a polycycloalkyl group; $R^2$ is methyl or ethyl, X is O or NH; and Y comprises a 5- or 6-membered heterocyclic ring having one or two nitrogens; or fused bicyclic heterocyclic rings having a total of three nitrogen atoms, one in each ring and one angular nitrogen.

3 Claims, No Drawings

CALCIUM INDEPENDENT CAMP PHOSPHODIESTERASE INHIBITOR ANTIDEPRESSANT

This is a division of application Ser. No. 07/984,190 filed Nov. 20, 1992, now U.S. Pat. No. 5,294,730; which is a division of Ser. No. 07/854,136 filed Mar. 19, 1992, now U.S. Pat. No. 5,196,426; which is a division of this application Ser. No. 07/696690, filed on May 30, 1991 now U.S. Pat. No. 5,128,358; which is a division of application Ser. No. 07/155,932 filed Jan. 19, 1988 as a request for U.S. Examination of International Application PCT/US/00958, filed Apr. 29, 1986.

BACKGROUND OF THE INVENTION

1. Field of the Invention

This invention relates to antidepressant agents having the formula

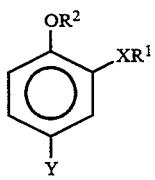

wherein $R^1$ is a polycycloalkyl group; $R^2$ is methyl or ethyl and Y is a saturated or unsaturated 5- or 6-membered nitrogen-containing heterocyclic ring or a fused bicyclic heterocyclic ring having three nitrogen atoms. More particularly it relates to such compounds wherein Y is a saturated or unsaturated 5- or 6-membered heterocyclic ring having one or two nitrogen atoms; or fused bicyclic heterocyclic rings having one nitrogen atom in each ring and one angular nitrogen.

2. Description of the Prior Art

U.S. Pat. Nos. 4,012,495 and 4,193,926, a continuation-in-part thereof, describe a series of 4-(polyalkoxyphenyl)-2-pyrrolidones having the formula (A)

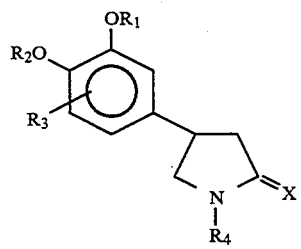

wherein $R_1$ and $R_2$ are hydrocarbon radicals of up to 18 carbon atoms or optionally substituted $(C_{1-5})$alkyl groups; $R_3$ is H or $OCH_3$; $R_4$ is H, alkyl, aryl or acyl, and X is O or S, which compounds have neuropsychotropic activity. Examples of hydrocarbon $R_1$ and $R_2$ groups are, inter alia, cycloalkyl and cycloalkylalkyl, preferably of 3 to 7 carbon atoms. Compounds related to those of formula (A) but substituted at the 1-position of the pyrrolidone ring with a —C)(O)R group where R is alkyl, aryl, aralkyl, amino or substituted amino group are disclosed as neuropsychotropic agents in U.S. Pat. No. 4,153,713.

A series of analogous compounds having formula (B)

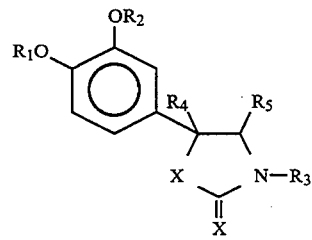

wherein $R_1$ and $R_2$ can be as defined above in formula (A); $R_3$ is hydrogen, optionally substituted alkyl, alkenyl, aryl, aralkyl or acyl; $R_4$ and $R_5$ can be hydrogen; and X is O or S are described in British Patent 1,588,639. They are alleged to exhibit central depressive, antidopaminergic, antinociceptive and anticonvulsant actions and to have a certain similarity to neuroleptics.

U.S. Pat. No. 4,308,278 discloses related compounds of formula (C) having anorexigenic activity

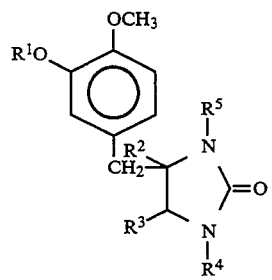

wherein $R^1$ is $(C_{3-6})$cycloalkyl or benzyl; each of $R^2$ and $R^3$ is hydrogen or $(C_{1-4})$alkyl; $R^4$ is $R^2$ or alkoxycarbonyl; and $R^5$ is hydrogen or alkoxycarbonyl. U.S. Pat. Nos. 3,636,039 and 3,923,833 a division thereof, disclose benzylimidazolidinones of formula (D) as hypertensive agents

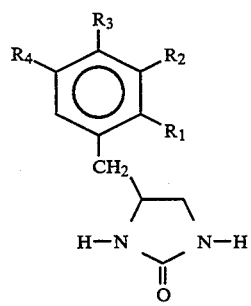

wherein variables $R_1$–$R_4$ are chosen from a variety of values including hydrogen and lower alkoxy.

Preparation of antihypertensive 1,4,5,6-tetrahydropyrimidines from appropriate benzaldehydes via intermediate glutaronitrile and glutaramide derivatives is described in U.S. Pat. No. 4,261,995.

SUMMARY OF THE INVENTION

The antidepressants of this invention have the formula (I)

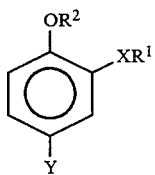

(I)

wherein R¹ is a polycycloalkyl group having from 7 to 11 carbon atoms;

R² is methyl or ethyl;

X is O or NH; and

Y comprises a 5- or 6-membered heterocyclic ring, especially a saturated or unsaturated 5- or 6-membered heterocyclic ring having one or two nitrogen atoms, said ring being optionally substituted with =O or =S, provided that when said optional group is present and the heterocyclic ring comprises one nitrogen atom the optional group is located on a carbon atom adjacent said nitrogen atom, and when the heterocyclic ring comprises two nitrogen atoms in a 1,3-position to one another said optional group is located on the carbon atom between the two nitrogen atoms; the nitrogen atoms of the heterocyclic rings which bear a hydrogen atom being optionally substituted with $(C_{1-5})$alkyl, $(C_{2-5})$ alkenyl, $(C_{1-5})$ alkanoyl, benzyl, phenylethyl or benzoyl; 1,2,3-thiadiazolyl 2,2-dioxide, the nitrogen atoms of which are optionally substituted with $(C_{1-5})$alkyl, $(C_{2-5})$alkenyl, $(C_{1-5})$alkanoyl, benzyl, phenylethyl or benzoyl; bicyclic heterocyclic moiety rings containing a total of three nitrogen atoms, one in each of the rings and one common to each ring (angular nitrogen).

Also included in this invention are pharmaceutically acceptable acid addition salts of formula (I) compounds which have a basic nitrogen atom. Further, pharmceutical compositions of formula (I) compounds and their use as antidepressant agents are embraced within the scope of this invention. Still further, processes for making formula (I) compounds and intermediates therefor, and the novel intermediates themselves are included in this invention. As will be recognized by those skilled in the art, stereocenters exist in several of the polycyclic (R¹) groups and heterocyclyl (Y) moieties of compounds of this invention. The racemic-diastereomeric mixtures and the individual optical isomers are also included in this invention.

As part of the present invention are certain compounds described herein which are especially useful as intermediates for preparation of formula (I) compounds. The compounds have formulae (IV), (V), (VII), (VIII), (IX), (XI), (XII), (XIII), (XIV) and (XVI) presented below. In the case of compounds of formulae (XI) and (XII), the tautomeric forms of said compounds are included in this invention, even though only one form, the ene form, is represented by said formulae.

Formula (I) compounds are characterized by a favorable therapeutic index and are significantly less emetic than are known compounds such as 4-[3-(cyclopentyloxy)-4-methoxyphenyl]-2-pyrrolidinone, which is described in U.S. Pat. No. 4,193,926, and which is known by the non-proprietary name of rolipram.

DETAILED DESCRIPTION OF THE INVENTION

More particularly this invention relates to formula (I) compounds wherein Y is

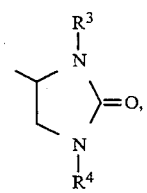 (a)

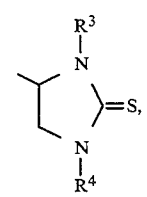 (b)

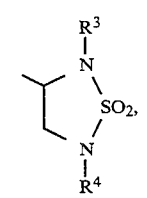 (c)

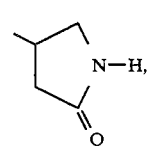 (d)

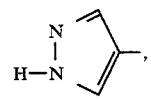 (e)

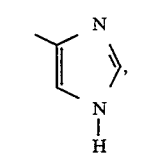 (f)

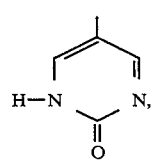 (g)

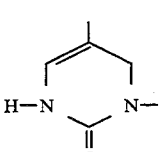 (h)

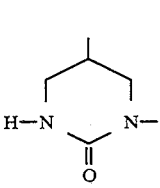 (i)

-continued

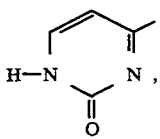 (j)

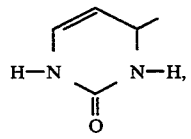 (k)

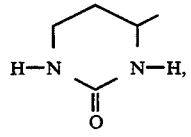 (l)

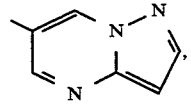 (m)

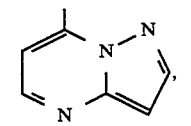 (n)

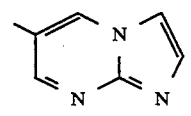 (o)

or

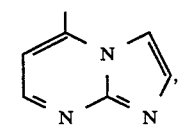 (p)

and $R^1$, $R^2$ and X are as defined above for formula I compounds; is hydrogen, $(C_{1-5})$alkyl, $(C_{2-5})$alkenyl, $R^3$ benzyl or phenethyl; and $R^4$ is hydrogen, $(C_{1-5})$alkyl, $(C_{1-5})$alkanoyl, optionally having a basic group, or benzoyl.

Examples of $R^1$ as $(C_{7-10})$polycycloalkyl are:
bicyclo[2.2.1]heptyl
bicyclo[2.2.2]octyl
bicyclo[3.2.1]octyl
tricyclo[5.2.1.0²·⁶]decyl
tricyclo[3.3.1.1³·⁷]decyl
indanyl.

Favored as values of $R^1$ are:
bicyclo[2.2.1]hept-2-yl
bicyclo[2.2.2]oct-2-yl
bicyclo[3.2.1]oct-3-yl
tricyclo[5.2.1.0²·⁶]dec-4-yl
tricyclo[5.2.1.0²·⁶]dec-8-yl
tricyclo[3.3.1.1³·⁷]dec-2-yl
indan-2-yl.

Preferred values of $R^1$ are bicyclo[2.2.1]hept-2-yl and indan-2-yl.

For each of the above categories the value of X as O and $R^2$ as methyl represent generally preferred compounds.

For a given value of $R^1$, favored values of Y are the 5-membered heterocyclyl rings, the bicyclic heterocyclic rings and the saturated 6-membered heterocyclic ring system. Preferred values of Y are the saturated 5- and 6-membered heterocyclic ring systems and the bicyclic heterocyclic zing systems (ring systems (a)–(d), (g), (l) and (m)–(p) above). Especially preferred are the heterocyclic ring systems (a), (g), (l) and (m)–(p).

From the standpoint of biological activity the exo isomer of a given compound of formula (I) is generally favored over the endo isomer because of greater potency. In actual practice in the case of formula (I) compounds having the asymmetric center in variables $R^1$ and/or Y, a mixture of the isomers of a given formula (I) compound is often favored because of relative ease of preparation of the mixture as compared to the pure isomers.

Products of this invention of formula (I) wherein X is O and Y represents heterocyclyl rings (a), (b) or (c) are prepared according to Sequence A:

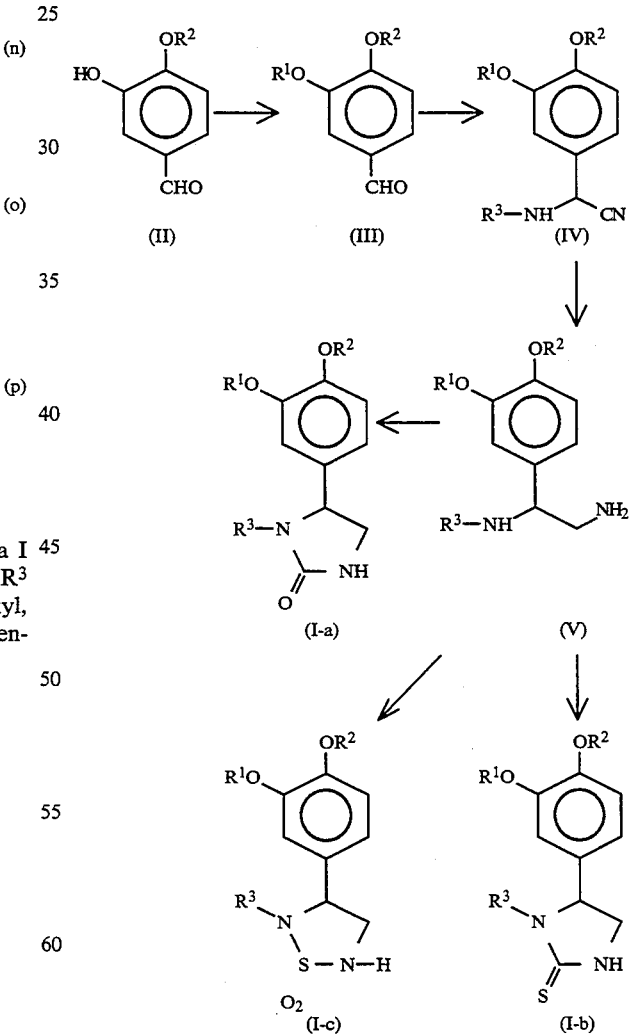

In sequence A, conversion of (II) to (III) is accomplished by the Williamson synthesis involving nucleophilic substitution of a phenoxide ion for halide ion. The known methodology comprises transformation of a phenolic reactant (II) to a phenoxide ion by reaction with a base, such as an alkali metal hydroxide or carbonate, in a reaction-inert colvent. By reaction-inert solvent is meant a solvent which does not react with starting materials, intermediates or product so as to adversely effect the yield of desired product. Suitable solvents are dimethylformamide, tetrahydrofuran, dioxan and bis(2-methoxyethyl)ether. The appropriate $R^1$ halide, preferably $R^1Br$ or $R^1Cl$, is reacted with the phenoxide ion at an elevated temperature, e.g., up to about 150° C., and the mixed ether (III) recovered by known procedures. In this reaction the use of the exo- or endo isomer of the polycycloalkyl halide results in production of an isomeric mixture of the corresponding ethers (III) which, if desired, can be separated by known procedures such as chromatography.

Alternatively, the mixed ethers of formula (III) are prepared by reacting the appropriate polycycloalkanol ($R^1$—OH) and phenol (II) in the presence of triphenylphosphine-diethyl azodicarboxylate as activator of the hydroxyl groups involved in the reaction. Reaction is conducted in a reaction-inert solvent such as tetrahydrofuran (THF) generally adding the diethyl azodicarboxylate at room temperature to a solution of polycycloalkanol, phenol and triphenylphosphine in THF. Upon completion of the addition, the reaction is refluxed until essentially complete and the mixed ether recovered by known procedures.

Still further, they are prepared from the appropriate polycycloalkanone by reacting it with catechol in a hydrocarbon solvent in the presence of p-toluenesulfonic acid under conditions which remove by-product water to produce the polycycloalkyl ketal. Lithium aluminum hydride/AlCl$_3$ reduction of the ketal affords the 2-polycycloalkyloxy phenol which is then brominated to give the 4-bromo-(2-polycycloalkyloxy)phenol, which is then converted to the OR$^2$ ether at the phenolic group. Replacement of the bromo function by formyl is achieved by treating it with tert-butyllithium in THF followed by quenching with N,N-dimethylformamide. All of the above mentioned reactions are carried out according to known procedures. Other starting materials required for this invention, if not available, or not previously described in the art, are prepared by known procedures such as those described herein.

The aminonitriles or cyanoamines of formula (IV) are produced by the Strecker synthesis which involves replacement of the carbonyl oxygen of (III) with amino, or substituted amino, and cyano groups. The procedure comprises simultaneous reaction of aidehyde (III) with the appropriate amine (or ammonia) as its hydrochloride salt and sodium cyanide in a reaction-inert solvent such as ethanol. The reaction proceeds in good yield at ambient temperatures and the product (IV) is recovered by known methods.

Formula (V) compounds are obtained by reduction of formula (IV) compounds. As is well known reduction of nitriles to amines can be carried out by a variety of means including catalytic hydrogenation over a noble metal or Raney nickel catalyst, by hydrides such as lithium aluminum hydride, diisobutylaluminum hydride, sodium diethylaluminum hydride and sodium bis(2-methoxyethoxy)aluminum hydride. A favored reducing agent in this invention is diisobutylaluminum hydride, (known as DiBal-H). The reduction is conveniently carried out by adding a solution of the cyano amine (IV) in a reaction-inert solvent, e.g. toluene, cyclohexane, diethyl ether, tetrahydrofuran, heptane, hexane and dichloromethane, to a solution of DiBal-H in a reaction-inert solvent, preferably in the same solvent as used for the cyanoamine. The reaction is conducted at a low temperature, e.g., below −50° C. during addition of the cyanoamine to the reducing agent, and for a period of time (2–4 hours, following completion of addition. It is then warmed slowly to about 0° C., excess reducing agent destroyed, and the product recovered by standard methods.

Cyclization of (V) to (I-a) wherein Y is a 2-imidazolidinon-5-yl group is achieved by treating the diamine (V) in a reaction-inert solvent with N,N′-carbonyldiimidazole or 1,1-carbonyldi-1,2,4-triazole in tetrahydrofuran or tetrahydrofuran-benzene at from 20° to 65° C. Phosgene can be used but because of its toxicity relative to the aforementioned cyclizing reagents, and the need for higher temperatures for cyclization is not favored. The corresponding thione of formula (I-b) wherein Y is a 2-imidazolidinthion-5-yl group is prepared in like manner but using N,N′-thiocarbonyldiimidazole as cyclizing agent. The formula (I-c) compounds wherein Y is a 1,2,3-thiadiazol-5-yl 2,2-dioxide are prepared by using sulfamide as cyclizing agent. Reaction is conducted in pyridine at reflux temperature until complete and the product recovered by known methods.

Compounds wherein Y of formula (II is heterocyclyl ring (f) and X is O are prepared according to sequence B:

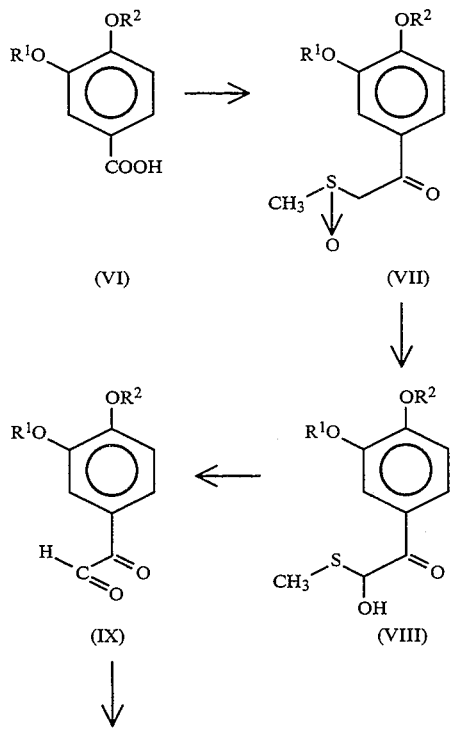

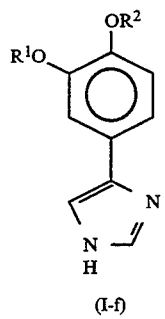

(I-f)

The formula (VI) reactants are prepared from compounds of formula (III) by procedures known to those skilled in the art. A convenient procedure comprises oxidation of (III) by means of Jones reagent chromic acid and sulfuric acid in water). The oxidant is added to the benzaldehyde reactant (III) in acetone at ambient temperature and the acid (VI) recovered by standard methods. The acid (VI) is next esterified by known procedures to, desirably, a lower alkyl ester and preferably the methyl ester. The ester is then reacted with about two equivalents of sodium methylsulfinylmethide (formed by reaction of sodium hydride with dimethyl sulfoxide) in tetrahydrofuran at from about 0°–10° C. to provide the beta-ketosulfoxide (VII). Isomerization of ketosulfoxide (VII) with aqueous acid results in rearrangement (Pummerer) of the sulfoxide to the hemimercaptal (VIII). Treatment of the hemimercaptal with cupric acetate monohydrate in a reaction-inert solvent such as chloroform affords the alpha-keto aldehyde (IX). The keto aldehydes of formula (IX) are readily transformed to formulae (I-f) compounds by reaction with formaldehyde and ammonium hydroxide in a reaction-inert solvent such as a lower alkanol, especially ethanol, at from abut 20° C. to 50° C. to provide the imidazoles. They are conveniently isolated as their acid addition salts.

Formula (I) compounds wherein X is O and Y is heterocyclyl rings (e), (g), (h), (i), (m) or (o) above are prepared according to sequence C:

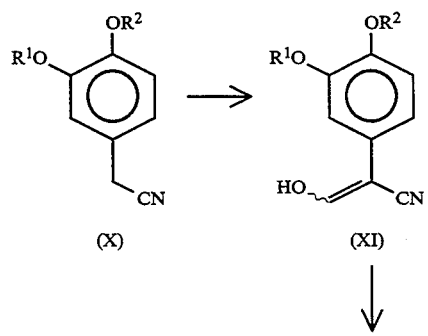

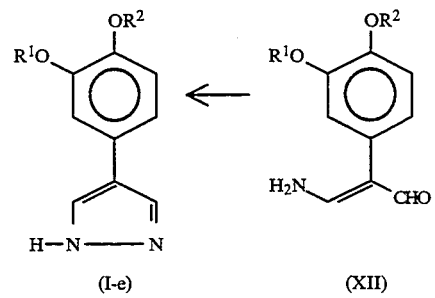

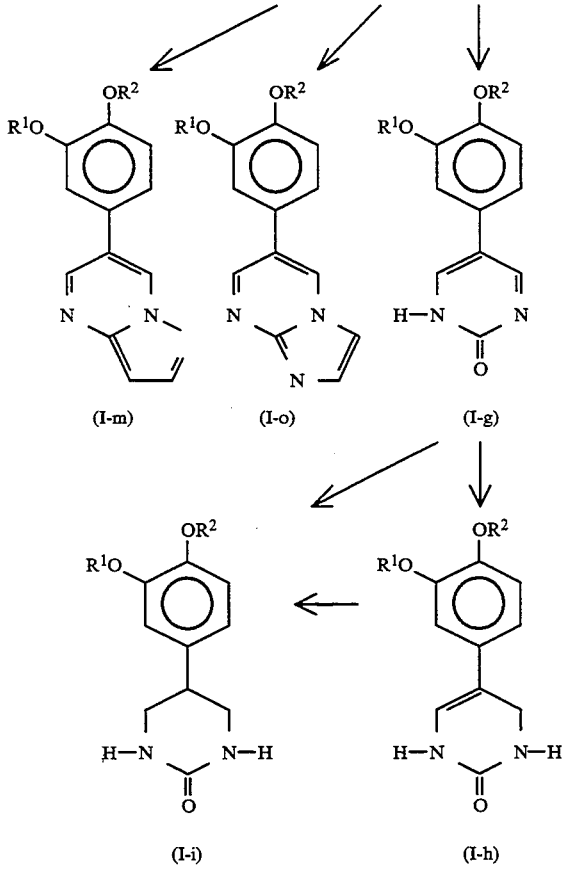

In sequence C reactants having formula (X) are prepared from formula (III) compounds by known procedures comprising reduction of the aldehyde function to hydroxymethyl by, for example, sodium borohydride, conversion of the alcohol to the corresponding bromo derivative by means of triphenylphosphine-carbon tetrabromide, and reaction of the thus-produced bromo derivative with alkali metal cyanide to afford (X). Reaction of (X) with ethyl formate in an aprotic reaction-inert solvent such as an aromatic or aliphatic hydrocarbon such as benzene, toluene or hexane; an ether such as dioxane, tetrahydrofuran, bis(2-methoxyethyl)ether; and in the presence of a base of sufficient strength, such as sodium hydride, to form an anion at the active methylene group provides formula (XI) compounds.

Conversion of (XI) to (XII) is accomplished by hydrogenation over Raney nickel in a reaction-inert solvent such as a lower alkanol, at pressures of from about 15 to about 100 psi (about 1 to about 7 kg/sq cm) at ambient temperature. Other catalysts such as noble metal catalysts can be used. However, their use may bring about reduction of the formyl group along with the nitrile group and is avoided. Cyclization of (XII) to (I-e) is readily carried out by treating the enamino-aldehyde (XII) with hydrazine in a lower alkanol solvent at about 50° to 100° C. The pyrazole derivative (e) is isolated by procedures known to the skilled artisan.

The 6-membered heterocyclyl structure (I-g) is produced by reaction of the enamino-aldehyde (XII) with urea in the presence of hydrochloric acid, or other strong acid, and in a reaction-inert solvent such as a lower alkanol or ethers such as dioxane, tetrafuran, bis (2-methoxyethyl) ether and 1,2-dimethoxyethane. The pyrimidinone (I-g) is then reduced to obtain (I-h) and/or (I-i). Reduction of (I-g) with Raney nickel in a reaction-inert solvent such as those enumerated above at a temperature of from about 50° C. to refluxing temperature of the chosen solvent, affords the tetrahydropyrimidinone (I-h). Further reduction over Raney nickel provides the hexahydropyrimidinone (I-i). In each of the above reductions a hydrogen pressure of from about 15 to about 100 psi is productive of satisfactory yields. Other catalysts such as noble metal catalysts can, of course, be used for these reductions, if desired.

Alternatively, compounds of formula (I-i) are prepared by reacting the appropriate 3-$R^1$O-4-$R^2$O- benzaldehyde of formula (III) with cyanoacetic acid in a reaction-inert solvent, e.g. pyridine, in the presence of piperidine, morpholine, piperazine, or other base which is more basic than pyridine, at from ambient temperature to about 120° C.; and preferably from 50° to 100° C. The 3-(3-$R^1$O-4-$R^2$O phenyl)glutaronitrile is isolated by known procedures as, for example, by pouring the reaction mixture in water and extracting the product with a suitable solvent, such as ethyl acetate. The glutaronitrile derivative is then converted to the corresponding glutaramide derivative by treatment in a reaction-inert solvent, e.g. aqueous acetone, with hydrogen peroxide and sodium carbonate at 0° C. The reaction mixture is slowly warmed to ambient temperature and stirred until complete. The diamide is recovered by concentration and extraction of the reaction mixture. The 3-(3-$R^1$O-4-$R^2$O)glutaramide is then cyclized by reaction in a reaction-inert solvent, e.g. pyridine, using lead tetraacetate at ambient temperature. The product is recovered by extraction.

Compounds of formulae (I-m) and (I-o) are produced from the enaminoaldehyde (XII) by reacting it with 3-aminopyrazole or a 2-aminoimidazole, respectively in the presence of a mineral acid. Ethanol is favored as a solvent although reaction-inert solvents such as are enumerated above for preparation of (I-g) can be used. The reaction is conducted at temperatures of from about 50° C. to the reflux temperature of the chosen solvent.

Formula (I) compounds wherein the heterocyclyl ring Y is (d) above are prepared as outlined in sequence D:

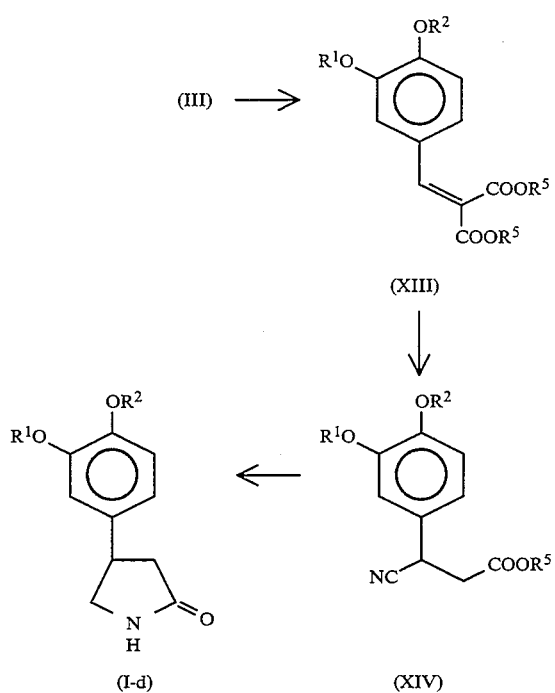

Knoevenagel condensation of aldehyde (III) with a di($C_{1-5}$)alkyl malonate, e.g., diethylmalonate, in a reaction-inert solvent, e.g., benzene, toluene, xylene, hexane, cyclic ethers, bis(2-methoxyethyl)ether, 1,2-dimethoxy ethane, in the presence of piperidine at 50°–150° C. yields the unsaturated diester (XIII). Reaction of the diester in ethanol or other reaction-inert solvent with sodium cyanide at ambient temperature gives the cyano ester (XIV). Reduction of the cyano ester in acetic acid using a noble metal catlayst, e.g., platinum oxide, affords the corresponding amino acid ester which is then cyclized to the corresponding alpha-carbethoxy lactam by heating in an aromatic hydrocarbon or ether solvent such as those mentioned above for the Knoevenagel condensation. Saponification of the carbethoxy lactam with ethanolic-alkali metal hydroxide at reflux and neutralization of the sodium salt thus produced provides the alpha-carboxy lactam which is thermally decarboxylated at about 180° C. to afford the pyrrolidone (I-d).

Sequence E below outlines preparation of formula (I) compounds wherein X is O and Y is heterocyclyl rings (j), (k), (l), (n) and (p):

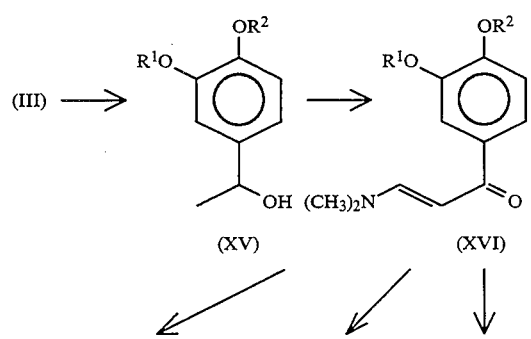

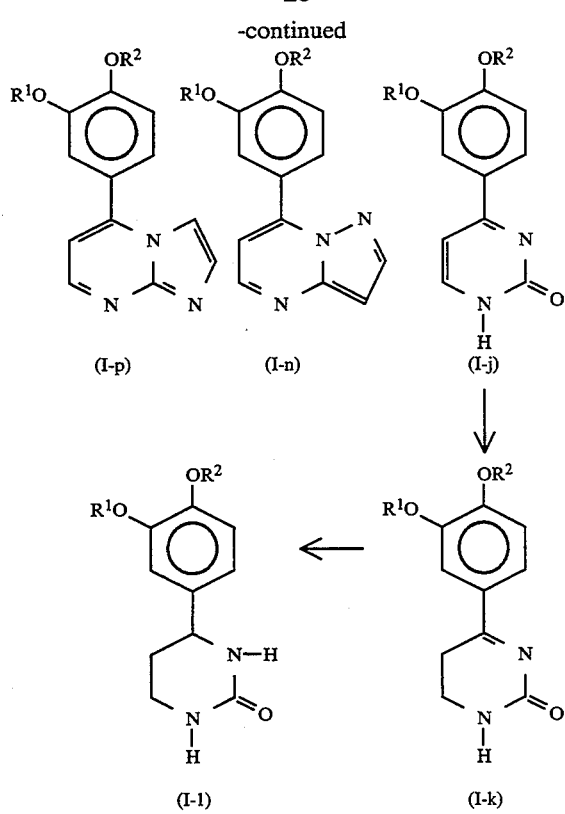

In this sequence a formula (III) compound is converted to carbinol (XV) by the well known Grignard reaction. The carbinol is then oxidized by means of Jones' reagent under conditions described above for Sequence B, formula (VI) compounds, to afford the corresponding ketone. Treatment of the ketone in tris-dimethylaminomethane, a reagent for introducing the dimethylaminoethylidene group, at the reflux temperature provides compounds of formula (XVI). This versatile reactant serves as the key building block for heterocyclyl compounds (I-j), (I-k), (I-l), (I-n), and (I-p) of this invention.

Reaction of (XVI) with urea in ethanolic hydrochloric acid affords (I-j) or a related compound wherein the heterocyclyl moiety is 4-(4-hydroxy-1,2,3,4-tetrahydro-2-pyrimidinone) of the formula

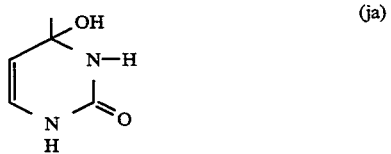

or a mixture of said two types of compounds. The product of the cyclization of urea with (XVI) depends upon the reaction time. Conduct of the reaction at or near reflux for about one hour affords principally the hydrated product wherein the heterocyclyl moiety is (ja). A heating period of about two hours yields a mixture of the two products in roughly equal amounts. A longer reaction period, e.g., 4 to 6 hours, gives (I-j) compounds, dehydrated derivatives of the (I-ja) compounds as major product.

Reduction of (I-j) compounds, e.g., with Raney nickel or a noble metal catalyst affords compounds of formula (I-k) or (I-l). The particular product depends upon the reduction conditions as those skilled in the art will recognize.

Compounds of formula (I-j) are produced from the precursor hydrated compounds wherein Y is (ja) by heating in ethanolic hydrochloric acid until removal of the elements of water is complete.

Compounds of formula (I-p) and (I-n) are readily obtained by reacting formula (XVI) compounds with 2-aminoimidazole or 3-aminopyrazole, respectively, under conditions corresponding to those presented above for preparation of (I-o) and (I-m).

Compounds of formula (I) wherein $XR^1$ is $-NH-R^1$ are prepared by procedures similar to those presented in the above reaction sequences. The difference resides in use of the appropriate 3-nitro-4-$OR^2$ benzaldehyde, 3-nitro-4-$OR^2$ benzylcyanide or 3-nitro-4-$OR^2$-benzoic acid, as starting material in place of the 3-$OR^1$-4-$OR^2$ diether reactants of sequences A-E. Said reactants are put through the above reaction sequences to provide compounds wherein the $-XR^1$ group of formula (I) compounds is replaced by nitro. Reduction of said nitro group to amino by known procedures, as by use of platinum oxide/hydrogen affords the corresponding amino derivative. Reductive alkylation of the amino derivative with the appropriate polycycloalkyl ketone according to procedures known to those skilled in the art affords the formula (I) compound in which the amino group $NH_2$ has been converted to $-NHR^1$.

Also of interest for the same utilities and in the same manner are formula I compounds wherein Y is one of the following heterocyclyl moieties:

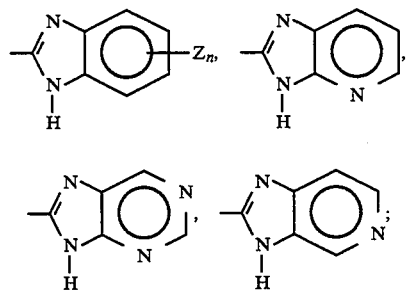

Z is hydrogen, $C_{1-4}$alkoxy, Cl; and n is 1 or 2. Said compounds are prepared according to the general procedure described in Indian J. Chem., 18B, 428 (1979). The procedure comprises reacting equimolar amounts of the 3-$R^1O$-4-$R^2O$ benzaldehyde of formula (III) above and the appropriate ortho-diamine of the 6-membered ring component of the fused ring system (e.g., 1,2-diaminobenzene) at 100° C. in nitrobenzene. The nitrobenzene serves as both solvent and oxidizing agent. Reaction is generally complete in 2-3 hours. The product is recovered by known methods, including flash column chromatography over silica gel.

The acid addition salts of formula (I) compounds having a basic group are readily prepared by adding a stoichiometric amount of the appropriate acid to a formula (I) compound in a solvent, preferably one in which the formula I) compound is at least partially soluble. The acid addition salt, if soluble in the solvent system is recovered by evaporation of the solvent or by addition of a non-solvent for the salt to precipitate it from the reaction solvent.

The compounds of this invention having formula (I) function as calcium independent c-AMP phosphodiesterase inhibitors and are useful as antidepressants. Their activity as calcium independent c-AMP phosphodiesterase inhibitors is determined by the method of Davis, Biochimica et Biophysica Acta. 797, 354–362 (1984). In this procedure, calcium-independent and dependent phosphodiesterases (IPDE and DPDE, respectively) are prepared from cerebral cortices of female Sprague-Dawley rats by first homogenizing the brain tissue in a pH 7.5 20 mM Tris-SCl buffer also containing 1 mM $MgCl_2$, 3 mM 2-mercaptoethanol, and 0.1 mM EGTA ethyleneglycol-bis-(beta-aminoethyl ether)-N,N'-tetraacetic acid). The homogenate is centrifuged at 105,000×g for 60 minutes, and the supernatant fluid containing the enzymes is passed through a column of Sephadex G-200 to separate IPDE from DPDE. The two phosphodiesterases are each further purified by affinity chromatography on a column of calmodulin-Sepharose.

Phosphodiesterase activity is determined using 0.1 ml reaction mixture containing Tris-HCl pH 7.5 buffer (5 umol), $MgCl_2$ (0.5 umol), and [$^3$H]cAMP (New England Nuclear, NET-275). The final concentration of cAMP is 1.0 uM (containing 400,000 dpm of [$^3$H]cAMP). Ten ul of vehicle or inhibitor solution and 10 ul of fresh IPDE or DPDE or the respective boiled enzymes are added to 80 ul of substrate in the Tris-HCl/$MgCl_2$ buffer. The reaction mixtures are incubated for 8 minutes at 37° C. and placed in a hot water bath for 2 minutes to stop hydrolysis of cAMP. Carrier 5'-AMP (0.5 ml of 0.5 mM 5'-AMP in 0.1M Hepes (N-2-hydroxyethylpiperazine-N'-2-ethanesulfonic acid)-0.1M NaCl pH 8.5 buffer) are added, and the contents of the incubation tubes placed on columns of polyacrylamide-boronate affinity gel (BIO-RAD Affi-Gel 601 Boronate Gel). The unreacted [$^3$H]cAMP eluted from the gel with 7.5 ml of the 0.1M Hepes-NaCl buffer. The [3M]cAMP eluted from the gel with 7.5 ml of the 0.1M Hepes-NaCl buffer. The [$^3$H]5'-AMP product is eluted with 7 ml of 50 mM Na acetate buffer pH 4.8. One-ml aliquots of the latter eluates are counted in a liquid scintillation counter to determine their content of radioactive 5'-AMP.

When used for the treatment of depression and other various neurological and psychic disorders, and characterized by withdrawal, anxiety, thought-disturbances and delusion, they are used as is or in the form of pharmaceutical compositions comprising a formula (I) compound and pharmaceutically-acceptable carriers or diluents. For oral administration, the preferred route for administering said compounds, suitable pharmaceutical carriers include inert diluents or fillers, therby forming dosage forms such as tablets, powders, capsules, and the like. These pharmaceutical compositions can, if desired, contain additional ingredients such as flavorings, binders, excipients and the like. For example, tablets containing various excipients, such as sodium citrate, are employed, together with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials therefor include lactose or milk sugar and high molecular weight polyethylene glycols.

For oral administration, the daily dose of active agent of formula (I) is from about 0.1 mg to about 10 mg., and for parenteral administration, preferably i.v. or i.m., from about 0.01 mg. to about 5 mg. The prescribing physician, of course, will ultimately determine the appropriate dose for a given human subject dependent upon factors such as the severity of the patient's symptoms and the patient's response to the particular drug.

The antidepressant activity of the compounds of this invention is determined by the behavioral despair paradigm described by Porsolt et al., Arch. Int. Pharmacodyn. 227, 327–336 (1977).

In this procedure a depressed state is induced in mice by forcing them to swim in a narrow water-containing cylinder from which there is no escape. The procedure involves injecting a mouse per os with the test compound and then (30 minutes post-injection) placing it in a standard 1 liter glass beaker containing 800 ml of 25 degree Centigrade water.

An observer then rates the animal's mobility (0=mobile; 1=immobile) every 30 seconds for 5 minutes beginning 2 minutes after being placed in the water. Male CD (Charles River) mice (10 per treatment) weighing 20-25 g are used as subjects. The compounds are administered in a solution (vehicle) containing 0.9% saline (90%), dimethyl sulfoxide (5%), and emul 4 (5%). All drugs are injected in a volume of 10 ml/kg. A vehicle treated mouse typically has a swim score of 9, while an antidepressant drug reduces the magnitude of immobility, resulting in a decrease in the swim score.

The second procedure is the method of Koe et al., J. Pharmacol. Exp. Therap. 226, 686–700 (1983) which comprises determination of the ability of a test drug to counteract reserpine hypothermia in mice. In this procedure, mice are placed in a room with an ambient temperature of 20° C. The mice are individually housed in plastic chambers with a cardboard bottom, injected with reserpine (1.0 mg/kg s.c.), and retained at 18°–19° C. for 18 hours. Their rectal temperatures are then ascertained, immediately after which they receive saline or drug treatment. Rectal temperatures are again measured, usually at 1, 2 and 4 hours after this second injection. Results are presented as the mean increase in reserpine-depressed temperature, expressed either as a percentage or an absolute increase. Typically, reserpine-pretreated mice given vehicle exhibit rectal temperatures averaging about 20°–22° C. 4 hours after vehicles. Treatment with desipramine mg/kg p.o.), a known antidepressant, yields temperatures averaging about 30°-33° C. (about a 40–50% increase). Administration of formula (I) compounds brings about an increase in rectal temperature of the test mice.

Formula (I) compounds are less emetic than is rolipram and afford, therefore, an advantage over rolipram. Their emetic behavior is determined by administering to dogs the test drug dissolved in ethanol at 10 mg/ml and dose diluted to final volume chosen with distilled water, the ethanol content of the final solution not exceeding 10%. The drug solution is administered via oral garage in a constant volume of 2 ml/kg body weight and the dogs then observed for emesis. If emesis occurs, the latency (the time from injection time to emesis) is recorded. If no emesis occurs within 30 minutes following administration of drug, a higher dose is administered to the next subject. A starting dose of 100 ug/kg was used based on the minimal effective dose of rolipram.

The following examples and preparations are provided solely for further illustration. The following abbreviations for peak shapes are used in reporting $^1$H-nmr values: bs, broad singlet; s, singlet; d, doublet; t, triplet;, q, quartet, m, multipier. In the Examples and Preparations no effort was made to optimize the yield of any given reaction,

EXAMPLE 1 alpha-N-Methylamino-3-(Bicyclo[2.2.1]hept-2-yloxy)-4-Methoxybenzene Acetonitrile The bicyclo[2.2.1]hept-2-yl ethers of Preparation Z (3.5 g, 0.014 mol) are dissolved in 50 ml of ethanol and to it is added sodium cyanide (0.736 g, 0.015 mol) and methylamine hydrochloride (1.0 g, 0.015 mol) and this is stirred for 18 hours at room temperature. The reaction mixture is diluted with saturated sodium bicarbonate solution and is extracted with, ethyl ether (3×30 ml). The combined organic layers are washed with saturated sodium chloride solution (3×30 ml), dried over anhydrous sodium sulfate, filtered and concentrated in vacuo to yield 4.15 g (~100%) of the cyanoamine as a clear oil. The cyanoamines are obtained as a 7:3 endo:exo mixture of bicycloalkyl ethers.

$^1$H Nmr (300 MHz, CDCl$_3$): delta 7.2–6.8 (m, 3H), 4.72 (bs, 1H), 4.6–4.7 (m, 0.7H) [endo], 4.2–4.3 (m, 0.3H) [exo], 3.9 (bs, 3H), 3.5 (m, 1H), 2.6 (bs, 3H), 2.7–1.0 (m, 10H).

In like manner the following conversions are carried out:

3-(Endo-tricyclo[5.2.1.0$^{2,6}$]dec-8-yloxy)-4-methoxybenzaldehyde is converted to the corresponding aminonitrile in 89.4% yield;

$^1$H NMR (300 MHz, CDCl$_3$): delta 7.1–6.81 (m, 3H), 4.7 (bs, 1H), 4.6 (m, 1H), 3.9 (s, 3H), 2.6 (s, 3H), 2.8–1.0 (m, 14H);

3-(exo-tricyclo[5.2.1.0$^{2,6}$]dec-4-yloxy)-4-methoxybenzaldehyde in 97.2% yield to the corresponding aminonitrile.

$^1$H NMR (300 MHz, CDCl$_3$): delta 7.1 (m, 2H), 6.9 (m, 1H), 4.9 (m, 1H), 4.75 (s, 1H), 3.9 (s, 3H), 2.65 (s, 3H), 2.6 (m, 2H), 2.3–1.2 (m, 12H);

3 -exo-benzobicyclo[2.2.1]hept-2-yloxy)-4-methoxybenzaldehyde in approximately quantitative yield to the corresponding aminonitrile:

$^1$H-NMR (300 MHz, CDCl$_3$): delta 7.4–6.9 (m, 7H), 4.6 (bs, 1H), 4.4 (m, 1H), 3.9 (s, 3H), 3.6 (bs, 1H), 3.4 (bs, 1H), 3.35 (bs, 1H), 2.5 (bs, 3H), 2.25 (m, 1H), 1.95 (m, 3H);

3-(endo-benzobicyclo[2.2.1]hept-2-yloxy)-4-methoxybenzaldehyde in quantitative yield to the corresponding aminonitrile;

$^1$H NMR (300 MHz, CDCl$_3$): delta 7.2–6.95 (m, 6H), 6.8 (m, 1H), 5.1 (m, 1H), 4.7 (bs, 1H), 3.7 (m, 1H), 3.61 (bs, 3H), 3.2 (m, 1H), 2.6 (s, 3H), 2.5 (m, 1H), 1.9 (m, 1H), 1.8 (m, 1H), 1.25 (m, 1H);

3-endo-tricyclo[3.2.1.0$^{2,6}$]dec-8-yloxy)-4-methoxybenzaldehyde to the corresponding aminonitrile in 95.4% yield:

$^1$H NMR (300 MHz, CDCl$_3$): delta 7.0–6.7 (m, 3H), 4.7 (m, 1H), 4.65 (bs, 1H), 3.87, 3.85 (s, 3H), [2-methoxyls], 2.5 (bs, 3H), 2.2–2.5 (m, 14H).

EXAMPLE 2

2-Methylamino-2-[3-(Bicyclo[2.2.1]hept-2-yloxy)-4-Methoxyphenyl]ethylamine

To a 1 liter flame dried round bottom flask is added di-isobutyl aluminum hydride (DiBal-H, 46.6 ml of a 1.5 molar solution in toluene, 0.07 mol) and 150 ml of dry toluene. The hydride solution is cooled to −78° C. and to it is added dropwise the cyanoamine of Example 2 (4.00 g, 0.014 mol) as a solution in 250 ml of dry toluene over a 1 hour period. The reaction is stirred at −78° C. for 2 hours and is warmed slowly to 0° C. where it is quenched slowly by the dropwise addition of a saturated solution of sodium potassium tartrate (10 ml). When gas evolution is no longer evident an additional 40 ml of the tartrate solution is carefully added and the reaction is warmed to room temperature. The reaction slurry is diluted with 150 ml ethyl ether and the aqueous layer is extracted with ethyl ether (2×50 ml). The combined ethereal layer is washed with saturated tartrate solution (2×50 ml), water (2×50 ml) and saturated sodium chloride solution (2×50 ml). The organics are dried over anhydrous sodium sulfate, filtered and concentrated in vacuo to yield 3.19 g (78.5%) of the diamine as a light yellow oil. The diamines are obtained as a 7:3 endo to exo mixture of bicyclo[2.2.1]hept-2-yloxy ethers.

In like manner, the following 2-methylamino-2-[3(R$^1$O)-4-methoxyphenyl]ethylamines are prepared from appropriate reactants:

R$^1$O=endo-benzobicyclo[2.2.1]hept-2-yloxy in 39% yield:

$^1$H NMR (300 MHz, CDCl$_3$): delta 7.2–6.7 (m, 7H), 5.2 (m, 1H), 3.7 (m, 1H), 3.6 (s, 3H), 3.2 (m, 2H), 2.85 (m, 2H), 2.5 (m, 1H), 2.4 (s, 3H), 1.9 (m, 1H), 1.8 (m, 1.2 (m, 1H);

R$^1$O=exo-benzobicyclo[2.2.1]hept-2-yloxy in 94.5% yield:

R$^1$O=endo-tricyclo[5.2.1.0$^{2,6}$]dec-4-yloxy in 96% yield:

$^1$H NMR (300 MHz, CDCl$_3$): delta 6.8–6.7 (m, 3H), 4.75 (m, 1H), 3.78 (s, 1H), 3.38 (m, 1H), 2.8 (m, 2H), 2.3 (s, 3H), 2.4–0.9 (m, 14H).

$^1$H NMR (300 MHz, CDCl$_3$): delta 6.7–7.0 (m, 4.6 (m, 0.7H), 4.2 (m, 0.3H), 3.8 (bs, 3H), 3.64 (bs, 1H), 3.33 (m, 1H), 2.7–2.85 (m, 2H), 2.3 (bs, 3H), 2.5–1.0 (m, 10H).

In like manner the following diamines are prepared from appropriate reactants: 2-methylamino-2-[3-(endo-tricyclo[5.2.1.0$^{2,6}$]dec-8-yloxy)-4-methoxyphenyl]ethylamine in approximately quantitative yield;

$^1$H NMR (300 MHz, CDCl$_3$): delta 7.0–6.8 (m, 3H), 5.7 (m, 1H), 3.9 (s, 3H), 3.5 (m, 1H), 3.0–1.0 (m, 19H).

2-Methylamino-2-[3-(endo-tricyclo[5.2.1.0$^{2,6}$]dec-4-yloxy)-4-methoxyphenyl]ethylamine in 76.62% yield.

EXAMPLE 3

1-Methyl-5-[3-(Bicyclo[2.2.1]hept-2-yloxy)-4-Methoxyphenyl)-2-Imidazolidinone

The diamines of Example 2 (3.19 g, 0.011 mol) are dissolved in dry tetrahydrofuran and treated with 1,1-carbonyldiimidazole (2.67 g, 0.0165 mol). The reaction is stirred for 24 hours at room temperature. The reaction mixture is poured into 50 ml of water and extracted with ethyl acetate (2×30 ml). The combined organics are washed with 1N sodium hydroxide solution (2×30 ml), 1N hyrochloric acid (2×30 ml), water (2×30 ml), and saturated salt solution (3×30 ml). The organics are dried over anhydrous sodium sulfate, filtered and concentrated in vacuo to a clear oil which is triturated with ether to yield 622 mg (17.8%) of the imidazolidinone as a white solid. MP: 142°–144° C. The material represents a mixture of 2 pairs of diastereoisomers.

$^1$H NMR (250 MHz, CDCl$_3$): delta 6.7–6.85 (m, 3H), 5.7 (bs, 1H), 4.6 (m, 0.7H), 4.4 (m, 1H), 4.2 (m, 0.3H), 3.82 (s, 2.1H), 3.80 (s, 0.9H), 3.68 (dd, J=11.5 Hz, J=8 Hz), 3.21 (dd, J=11.5, J=8.1 Hz), 2.6 (s, 3H), 2.6–1.0 (m, 10 Hz).

$^{13}$C NMR (63HH$_2$, CDCl$_3$): delta 163.2, 149.8, 148.7, 131.7, 119.3, 113.2, 112.3, 112.2, 112.0, 78.9, 78.8, 62,84, 62.81, 56.15, 56.0, 47.5, 41.1, 40.5, 39.9, 37.2, 37.1, 36.7, 35.4, 35.3, 29.4, 28.74, 28.70, 28.3, 24.2, 20.7 (30 lines).

MS: M+ = 316.0, 222.1, 95

Similarly, the following imidazolidinones are prepared by cyclization of appropriate diamines: 1-methyl-5-[3-(endo-tricyclo[5.2.1.0$^{2.6}$]dec-8-yloxy)-4-methoxyphenyl]-2-imidazolidinone in 20.7% yield.

MP = 149°–152° C.

1H NMR (300 MHz, CDCl$_3$): delta 6.9–6.8 (m, 3H), 5.15 (bs, 1H), 4.65 (m, 1H), 4.5 (m, 1H), 3.9 (s, 3H), 3.75 (m, 1H), 3.25 (m, 1H), 2.7 (s, 3H), 2.8–1.0 (m, 14H).

|   | Analysis: | |
|---|---|---|
|   | Calcd | Act. |
| C | 70.76 | 70.72 |
| H | 7.92 | 7.86 |
| N | 7.86 | 7.79 |

1-methyl-5-[3-(exo-tricyclo[5.2.1.0$^{2.6}$]dec-4-yloxy)-4-methoxyphenyl]-2-imidazolidinone in 11.42% yield.

1H NMR (300 MHz, CDCl$_3$): delta 6.8 (m, 3H), 6.1 (bs, 1H), 4.8 (m, 1H), 4.4 (m, 1H), 3.8 (bs, 3H), 3.7 (m, 1H), 3.2 (m, 1H), 2.6 (s, 3H), 3.6–1.2 (m, 14H).

$^{13}$C NMR (75.43 MHz, CDCl$_3$): delta 163.3, 150.1, 148.2, 131.9, 119.6, 113.6, 112.1, 83.4, 56.0, 47.5, 43.2, 42.3, 40.6, 32.7, 29.6, 28.7, 23.2 (17 lines).

Analysis Calcd. for C$_{21}$H$_{28}$N$_2$O$_3$: C, 70.75; H, 7.91; N, 7.86. C, 68.76; H, 7.61; N, 8.35.

1-methyl-5-[3-(endo-benzobicyclo[2.2.1]hept-2-yloxy)-4-methoxyphenyl]-2-imidazolidinone in 13.74% yield:

$^1$H NMR (300 MHz, CDCl$_3$): delta 7.2–7.05 (m, 4H), 6.8 (m, 3H), 5.1 (m, 1H), 4.85 (bs, 1H), 4.45 (m, 1H), 3.7 (m, 1H), 3.68 (m, 1H), 3.4 (m, 1H), 3.25 (m, 1H), 2.65 (s, 1H), 2.45 (m, 1H), 1.9 (m, 1H), 1.8 (m, 1H), 1.25 (m, 1H);

1-methyl-5-[3-(exo-benzobicyclo[2.2.1]hept-2-yloxy)-4-methoxyphenyl]-2-imidazolidinone in about 17% yield:

$^1$H NMR (300 MHz, CDCl$_3$): delta 7.2–7.1 (m, 4H), 7.0–6.9 (m, 3H), 4.5 (m, 1H), 4.4 (m, 1H), 3.9 (s, 1H), 3.75 (m, 1H), 3.6 (bd, 1H), 3.4 (bs, 1H), 3.25 (m, 1H), 2.67+2.65 (s, 3H), 2.25 (m, 1H), 1.95 (m, 1H).

Analysis Calcd. for C$_{22}$H$_{24}$N$_2$O$_3$: C, 72.50; M, 6.63; N, 7.68. Found: C, 71.73; M, 6.78; N, 7.28.

1-methyl-5-[3-(endo-tricyclo[5.2.1.0$^{2.6}$]dec-4-yloxy)-4-methoxyphenyl]-2-imidazolidone in 7.2% yield:

$^1$H NMR (300 MHz, CDCl$_3$): delta 6.8–6.7 (m, 3H), 5.75 (bs, 1H), 4.75 (bs, 1H), 4.42 (m, 1H), 3.83 (s, 3H), 3.72 (m, 1H), 3.28 (m, 1H), 2.65 (s, 3H), 2.3–0.9 (m, 14H).

$^{13}$C NMR (75.4 MHz, CDCl$_3$): delta 163.2, 150.8, 147.8, 131.8, 120.0, 114.5, 112.4, 82.5, 62.8, 56.2, 47.6, 46.2, 40.4, 37.7, 31.8, 28.8, 28.5 (17 lines).

Analysis Calcd. for C$_{21}$H$_{28}$N$_2$O$_3$: C, 70.75; H, 7.91; N, 7.86. Found: C, 69.74; H, 7.93; N, 7.48.

EXAMPLE 4

1-n-Butyl-3-Methyl-4-[3-(Bicyclo[2.2.1]hept-2-yloxy)-4-Methoxyphenyl]-2-Imidazolidinone The imidazolidinone of Example 3 [0.5 g, 1.58 mmol) is dissolved in 20 ml THF and 5 ml DMG, treated with sodium hydride (41 mg, 1.73 mmol), cooled to 0° C. and treated with n-iodobutane (0.581 g, 3.15 mmol). The reaction is warmed slowly to room temperature and stirred for 24 hours. It is then diluted with water, and extracted with ether. The organic layer is washed with water, brine, dried over MgSO$_4$, filtered and concentrated in vacuo. The product is triturated with ether to afford 211 mg (35.8%) of the product. This material is 7:3 endo/exo isomer mixture.

Analysis Calcd. for C$_{22}$H$_{32}$N$_2$O$_3$: C, 70.93; H, 8.66; N, 7.52. Found: C, 69.95; H, 8.66; N, 7.43.

EXAMPLE 5

1-Acetyl-3-Methyl-4-[3-(Bicyclo[2.2.1]hept-2-yloxy)-4-Methoxyphenyl)-2-Imidazolidinone Repetition of the procedure of Example 4, but using an appropriate amount of acetyl chloride in place of n-iodobutane affords the title compound in 29.3% yield.

Analysis (as hemihydrate): Calcd. for C$_{20}$H$_{26}$N$_2$O$_4$.½ H$_2$O:

C, 65.44; H, 7.41; N, 7.63. Found: C, 65.36; H, 7.29; N, 7.00.

EXAMPLE 6

1,3-Dimethyl-4-[3-(Bicyclo[2.2.1]hept-2-yloxy)-4-Methoxyphenyl]-2-Imidazolidinone Repetition of the procedure of Example 4 but using a stoichiometric amount of iodomethane in place of n-iodobutane provides the title compound in 56.3% yield.

Analysis: Calcd. for C$_{19}$H$_{26}$N$_2$O$_3$: C, 68.86; H, 7.90; N, 8.45. Found: C, 68.57; H, 7.87; N, 8.14.

EXAMPLE 7

2-Methyl-3-3-[3-(bicyclo[2.2.1]hept-2-yloxy)-4-methoxyphenyl]-1,2,5-thiadiazolidine 1,1-Dioxide The dimine of Example 2 (3.3 g, 11.37 mmol) are dissolved in 180 ml dry pyridine and are treated with sulfamide (1.36 g, 14.22 mmol). The reaction mixture is warmed to reflux and is refluxed for 15 hours. The reaction is cooled to room temperature and is diluted with 500 ml of ethyl ether and is washed with 5×100 ml H$_2$O, 5×100 ml 1 normal HCl and 2×200 ml water. The organics are dried over anhydrous sodium sulfate, filtered and concentrated in vacuo. The crude residue is chromatographed on SiO$_2$ with 50% ethyl acetate/hexanes as the eluent. The appropriate fractions are collected, and concentrated to yield 1.35 g (33.7%) of the cyclic sulfamides as an orange solid.

MP: 55.57° C.

$^1$H NMR (300 MHz, CDCl$_3$): delta 6.85–6.7 (m, 3H), 4.7–4.5 (m, 1.5H), 4.3–4.1 (m, 1.5H), 3.8 (bs, 3H), 3.65 (m, 1H), 3.3 (m, 1H), 2.51 (bs, 3H), 2.6–1.0 (m, 10H).

HRMS 352.1457 (M+) calcd. for C$_{17}$H$_{24}$N$_2$O$_4$S, 352.1466.

EXAMPLE 8

1-Methyl-5-[3-(Bicyclo[2.2.1]hept-2-yloxy)-4-Methoxyphenyl]-2-Imidazoldinethione The diamines of Example 2 (2.3 g, 7.93 mmol) are dissolved in 65 ml of tetrahydrofuran and treated with N,N-thiocarbonyl imidazole (1.76 g, 9.91 mmol). The reaction is stirred for 41 hours at room temperature. The reaction is worked up by dilution with 250 ml of ethyl ether. The collected organics are washed with 1×80 ml water, 2×100 ml 0.5N NaOH solution, 2×100 ml 0.5N HCl solution, 1×100 ml water. The organics are dried over anhydrous magnesium sulfate, filtered and concentrated in vacuo. The crude residue is purified by flash silica gel chromatography with 50% ethyl acetate/hexanes as the eluent. The appropriate fractions are collected and concentrated to yield 1.70 g (65.5%) a 7:3 endo:exo mixture of the thioimidazolidinone as a light yellow solid.

MP: 149°–150.5° C.

$^1$H NMR (250 MHz, CDCl$_3$): delta 6.9–6.7 (m, 3H), 6.15 (bs, 1H), 4.7 (m, 1H), 4.6 (m, 0.7H), 4.2 (m, 0.3H), 3.9 (m, 3H), 3.86 (s, 2.1H), 3.83 (s, 0.9H), 3.42 (m, 1H), 2.93 (bs, 3H), 2.6–1.1 (m, 10H).

HRMS 332.1559 (M+) Calcd. for C$_{18}$H$_{24}$N$_2$SO$_2$ 332.1583.

EXAMPLE 9 alpha-N-Methylamino-3-(Exo-Bicyclo[2.2.1]hept-2-yloxy)-4-Methoxybenzene acetonitrile 3-(exo-bicyclo[2.2.1]hept-2-yloxy)-4-methoxybenzaldehyde (4.22 g, 17.0 mmol) is dissolved in 60 ml of ethanol and is treated with methylamine hydrochloride (1.40 g, 21.27 mmol) and sodium cyanide (1.04 g, 21.27 mmol). To the reaction is added 15 ml of water to make the mixture homogeneous. The reaction is stirred at room temperature for 72 hours. The reaction is worked up by dilution with 250 ml of ethyl ether and is washed with 3×100 ml water and 1×100 ml saturated sodium chloride solution. The organics are dried over magnesium sulfate, filtered and concentrated in vacuo to yield 4.45 g (91%) of the amino-nitrile as a clear light yellow oil.

$^1$H NMR (300 MHz, CDCl$_3$): delta 7.1–6.8 (m, 3H), 4.7 (bs, 1H), 4.25 (m, 1H), 3.88 (s, 3H), 2.56 (s, 3H), 2.5–1.0 (m, 10H).

EXAMPLE 10

2-Methylamino-2-[3-(Exo-bicyclo[2.2.1]hept-2-yloxy)-4-Methoxyphenyl]ethylamine

The exo-bicyclo[2.2.1]hept-2-yloxy-aminonitrile of Exmple 9 (4.45 g, 15.56 mmol) is dissolved in 100 ml of dry toluene and is added to a −78° C. solution of Dibal-H (70.01 mmol) in 300 ml toluene. The reaction is stirred at −78° C. for 4 hours. The cooling bath is removed and the reaction is quenched slowly dropwise with 100 ml of a saturated sodium/potassium tartrate solution. The reaction is warmed slowly to room temperature and is diluted with 500 ml of ethyl acetate. The layers are separated and the aqueous layer is saturated with sodium chloride and extracted 1×100 ml methylene chloride. The collected organics are washed with 1×100 ml saturated sodium/potassium tartrate solution and 2×100 ml saturated sodium chloride solution. The organics are dried over potassium carbonate filtered and concentrated in vacuo to yield 4.0 g (90%) of the exo-bicyclo[2.2.1]hept-2-yloxy-diamine as a clear viscous oil.

$^1$H NMR (300 MHz, CDCl$_3$): delta 6.83 (m, 3H), 4.22 (bd, 1H), 3.83 (s, 3H), 3.38 (m, 1H), 2.84 (m, 2H), 2.3 (s, 3H), 2.5–1.0 (m, 10H).

EXAMPLE 11

1-Methyl-5-[3-Exo-bicyclo[2.2.1]hept-2-yloxy)-4-Methoxyphenyl]-2-Imidazolidinone The exo-bicyclo[2.2.1]hept-2-yloxy-diamine of Example 10 (4.0 g, 13.79 mmol) is dissolved in 170 ml of tetrahydrofuran and is treated with N,N-carbonyldiimidazole (2.8 g, 17.24 mmol). The reaction is stirred for 40 hours at room temperature. The reaction mixture is worked up by dilution with 300 ml of ethyl ether and is washed with 1×100 ml of water, 1×100 ml of 0.5N sodium hydroxide solution, 1×100 ml 0.5N HCl solution and 1×100 ml H$_2$O. The organics are dried over sodium sulfate, filtered and concentrated in vacuo. The residue is purified on silica gel flash chromatography with 50% ethyl acetate/hexanes as the eluent. The appropriate fractions are collected and concentrated in vacuo to yield 1.60 g (36.7%) of the imidazolidinone as a white powder. MP 148°–151° C.

$^1$H NMR (300 MHz, CDCl$_3$): delta 6.8 (m, 3H), 5.3 (3, 1H), 4.4 (m, 1H), 4.2 (bd, 1H), 3.80 (s, 3H), 3.68 (dd, J=11.5 Hz, J=8 Hz), 3.21 (dd, J=11.5 Hz, J=8.1 Hz), 2.6 (s, 3H), 2.5–1.0 (m, 10 Hz).

$^{13}$C NMR (63 MHz, CDCl$_3$): delta 163.12, 150.03, 147.63, 131.67, 119.43, 119.35, 112.92, 112.82, 112.02, 81.04, 62.74, 56.0, 47.46, 41.0, 39.79, 35.33, 35.23, 28.63, 28.25, 24.15 (20 lines).

HRMS 316. 1816 (M+) Calcd. for C$_{18}$H$_{24}$N$_2$O$_3$ 316.1787.

EXAMPLE 12 alpha-N-Methylamino-3-(Endo-Bicyclo[2.2.1]hept-2-yloxy)-4-Methoxybenzene Acetonitrile The aminonitrile is prepared from the aldehyde (Preparation AA) (3.46 g, 14.06 mmol) according to the procedure of Example 1 to produce 3.8 g (95%) of the product.

$^1$H NMR (300 MHz, CDCl$_3$): delta 7.0–6.75 (m, 3H), 4.62 (bs, 1H), 4.7–4.5 (m, 1H), 3.82 (s, 3H), 2.65 (m, 1H), 2.6 (bs, 3H), 2.3 (m, 1H), 2.05 (m, 2H), 2.2–1.1 (m, 6H).

EXAMPLE 13

2-Methylamino-2-[3-[Endo-Bicyclo[2.2.1]hept-2-yloxy)-4-Methoxyphenyl]ethylamine

The diamine is prepared according to the procedure of Example 2 from the aminonitrile (3.8 g, 13.28 mmol) of Example 12 to produce 3.9 g (~100%) of the product.

$^1$H NMR (300 MHz, CDCl$_3$): delta 6.9–6.7 (m, 3H), 4.7 (m, 1H), 3.91 (s, 3H), 3.96 (m, 1H), 2.96 (m, 2H), 2.6 (m, 1H), 2.3 (bs, 3H), 2.3–1.0 (m, 9H).

EXAMPLE 14

1-Methyl-5-[3-(Endo-Bicyclo[2.2.1]hept-2-yloxy)-4-Methoxyphenyl]-2-Imidazolidinone The imidazolidinone is prepared from the diamine of Example 13 (3.9 g, 13.44 mmol) according to the method of Example 4 to afford 1.6 g (38%) of the product as a white solid. MP: 148°–149.5° C.

$^1$H NMR (300 MHz, CDCl$_3$): delta 6.85–6.65 (m, 3H), 4.6 (m, 1H), 4.45 (m, 1H), 3.83 (s, 3H), 3.68 (m, 1H), 3.2 (m, 1H), 2.6 (s, 3H), 2.55 (m, 1H), 2.3–1.1 (m, 9H).

$^{13}$C NMR (63 MHz, CDCl$_3$): delta 163.1, 149.9, 148.8, 131.7, 119.3, 112.4, 112.26, 112.11, 79.01, 62.82, 62.84, 56.21, 47.5, 40.61, 37.26, 37.23, 37.13, 36.77, 29.42, 28.76, 28.73, 27.32, 29.74 (23 lines).

Some doubling due to remote diastereomers.

EXAMPLE 15 alpha-N-Methylamino-3-(bicyclo[2.2.2]oct-2-yloxy)-4-Methoxybenzene Acetonitrile

The bicyclo[2.2.2]octylether of Preparation BB (3.30 g, 12.7 mmol) is dissolved in 50 ml of ethanol and to this is added methylamine hydrochloride (1.28 g, 19 mmol)

and sodium cyanide (930 mg, 19 mmol). To this suspension is added dropwise water until the reaction mixture becomes clear. The reaction is stirred for 15 hours and is then treated with additional methylamine hydrochloride (320 mg, 4.75 mmol) and sodium cyanide (232 mg, 4.75 mmol). The reaction is stirred for 24 hours at room temperature. The reaction is diluted with 250 ml H$_2$O and 250 ml ethyl ether. The resulting aqueous layer was re-extracted with 100 ml ether and the combined organics are washed with 1×200 ml 1N NaOH solution, 2×200 ml water and 1×100 ml brine. The organics are dried over magnesium sulfate, filtered and concentrated in vacuo to yield 3.80 gram (~100%) of the aminonitrile as a viscous oil. It was used in Example 16 without further purification.

EXAMPLE 16

2-Methylamino-2-[3-(bicyclo[2.2.1]oct-2-yloxy)-4-Methoxyphenyl]ethylamine

To a solution of Dibal-H (64.5 mmol) in 140 ml of toluene at −78° C. is added dropwise the cyanoamine (3.80 g, 12.7 mmol) of Example 15 over a 1 hour period as a solution in 50 ml toluene. After the addition is complete the reaction is stirred for an additional 1.5 hours at −78° C. The reaction mixture is quenched at −78° C. with a saturated solution of sodium potassium tartrate (5 ml) and allowed to warm slowly to room temperature. The reaction is then treated dropwise with an additional 100 ml of saturated sodium potassium tartrate solution and is stirred for 15 hours. The suspension is diluted with 100 ml ethyl acetate. The aqueous layer is saturated with sodium chloride and extracted 2×100 ml ethyl acetate. The collected organics are washed with brine dried over magnesium sulfate, filtered and concentrated in vacuo to yield 3.14 g (81%) of the aryldiamine as a viscous oil. It was used as is in the procedure of Example 17.

EXAMPLE 17

1-Methyl-5-[3-Bicyclo[2.2.1]oct-2-yloxy)-Methoxyphenyl]-2-Imidazolidinone

The aryldiamine (3.14 g, 10.3 mmol) of Example 16 is dissolved in 100 ml of dry tetrahydrofuran is treated with N,N-carbonyldiimidazole (2.09 g, 12.9 mmol) and is stirred at room temperature for 90 hours. The reaction mixture is diluted with 200 ml of ethyl ether and is washed with 1×50 ml 2.5% HCl solution, 1×50 ml water, 1×50 ml 1N NaOH solution, 1×50 ml H$_2$O and 1×50 ml brine. The organics are dried over MgSO$_4$, filtered and concentrated in vacuo. The residue is chromatographed on SiO$_2$ (32-64) with 20% hexane/80% ethyl acetate as the eluent. The appropriate fractions are collected and concentrated in vacuo to yield 1.10 g (32%) of the imidazolidinone as a white solid. MP: 142°-146° C.

$^1$H NMR (300 MHz, CDCl$_3$): delta 6.85-6.65 (m, 3H), 5.4 (bs, 1H), 4.45-4.3 (m, 2H), 3.8 (s, 3H), 3.65 (m, 1H), 3.2 (m, 1H), 2.55 (bs, 3H), 2.1-1.2 (m, 12H).

$^{13}$C NMR (75.6 MHz, CDCl$_3$): delta 163.2, 163.14, 150.46, 150.43, 147.9, 131.7, 119.68, 119.63, 113.54, 113.4, 112.3, 76.24, 76.18, 62.86, 62.80, 62.76, 56.22, 47.61, 34.86, 28.80, 28.41, 25.37, 24.62, 23.42, 19.21 (25 lines). Some doubling due to remote diastereomers.

HRMS 330.1943 (M+) calculated for C$_{19}$H$_{26}$N$_2$O$_3$ 330.1924 (M+) calculated to C$_{19}$H$_{26}$N$_2$O$_3$ 330.1924.

EXAMPLE 18 alpha-N-Methylamino-3-(Exo-Bicyclo[3.2.1.]oct-2-yloxy)-4-Methoxybenzene Acetonitrile The aryl ether aldehyde of Preparation CC (1.68 g, 6.46 mmol) is dissolved in 50 ml of ethanol and is treated with sodium cyanide (0.379 g, 7.75 mmol) and methylamine hydrochloride (0.519 g, 7.75 mmol). The reaction is stirred for 24 hours at room temperature. The reaction is made basic with saturated NaHCO$_3$ solution and is diluted with 50 ml of water. The aqueous layer is extracted 3×30 ml ethyl ether. The combined organics are washed with 2×30 ml water and 2×30 ml brine, dried over Na$_2$SO$_4$, filtered and concentrated in vacuo to yield 1.65 g (89.5%) of the aminonitrile as a clear orange oil.

$^1$H NMR (300 MHz, CDCl$_3$): delta 7.05-6.75 (m, 3H), 4.65 (bs, 1H), 4.45 (m, 1H), 3.83 (s, 3H), 2.55 (bs, 3H), 2.3 (m, 1H), 2.05 (m, 1H), 1.8-1.3 (m, 10H).

EXAMPLE 19

2-Methylamino-2-[3-(Exo-Bicyclo[3.2.1]oct-2-yloxy)-4-Methoxyphenyl]ethylamine

A solution of diisobutyl aluminum hydride (20.25 ml of a 1.5 molar solution in toluene, 0.028 mol) in 200 ml of dry toluene is cooled to −78° C. and is treated dropwise with a solution of the aminonitrile of Example 18 (1.65 g, 5.76 mmol) in 25 ml of toluene. The addition is completed in 15 hours and the reaction is stirred at −78° C. for 2 hours. The reaction is warmed to 0° C. and is quenched with 50 ml of a saturated sodium potassium tartrate solution. The organic layer is separated and the aqueous layer is extracted 3×30 ml ether. The combined organics are washed with 3×30 ml dilute sodium potassium tartrate solution, 3×30 ml brine. The organics are dried over NaSO$_4$, filtered and concentrated in vacuo to yield 0.95 g (54.5%) of the diamine as a clear yellow oil.

$^1$H NMR (300 MHz, CDCl$_3$): delta 6.9-6.75 (m, 3H), 4.45 (m, 1H), 3.8 (s, 3H), 3.4 (m, 1H), 2.85 (m, 2H), 2.32 (s, 3H), 2.2-1.4 (m, 12H).

EXAMPLE 20

1-Methyl-5-[3-(Exo-Bicyclo[2.2.1]oct-2-yloxy)-4-Methoxylphenyl]-2-Imidazolidinone The aryl diamine of Example 19 (0.95 g, 3.14 mmol) is dissolved in 30 ml of dry tetrahydrofuran and is treated with N,N-carbonyldiimidazole (0.76 g, 4.71 mmol). The reaction is stirred for 18 hours at room temperature and is then diluted with 30 ml water and 30 ml ethyl acetate. The aqueous layer is separated and extracted 2×20 ml ethyl acetate. The combined organics are washed with 2×20 ml in NaOH solution, 2×20 ml 1N HCl, 2×20 ml water and 2×20 ml brine. The organic layer is dried over Na$_2$SO$_4$, filtered and concentrated vacuo to yield a white slurry. Purification by titration with 3×50 ml ether to yield 214 mg (20.6%) of the imidazolidinone as a white solid. MP: 145°-147° C.

$^1$H NMR (300 MHz, CDCl$_3$): delta 6.9-6.7 (m, 3H), 4.5-4.3 (m, 2H), 3.83 (s, 3H), 3.7 (m, 1H), 3.24 (m, 1H), 2.62 (s, 3H), 2.3 (m, 1H), 2.05 (m, 1H), 1.8-1.3 (m, 10H).

HRMS 330.1962 (M+) Calcd for C$_{19}$H$_{26}$N$_2$O$_3$ 330.1943.

EXAMPLE 21

5-[3-(Bicyclo[2.2.1]hept-2-yloxy]-4-Methoxyphenyl]2,4-Imidazolidinedione 3-(Bicyclo[2.2.1]hept-2-yloxy)-4-Methoxybenzaldehyde (20.0 g, 81.3 mmol), sodium cyanide (8.0 g, 162.6 mmol) and ammonium carbonate (32.0 g, 333.3 mmol) are dissolved in 100 ml ethanol and 100 ml water and refluxed for 4 hours. The reaction is cooled, neutralized with 1N HCl solution and the product extracted 2×ethyl acetate. The collected organics are washed with water, brine and concentrated in vacuo. The solid isredissolved in ethyl acetate, dried over $Na_2SO_4$, concentrated in vacuo and the resulting crude oil triturated from ether to produce 18.3 g (71%) of the hydantoin as a crystalline material. This material is a 7:3 endo/exo mixture of bicycloalkyl isomers.

$^1$H NMR (300 MHz, DMSO): delta 7.4–6.8 (m, 3H), 5.3 (m, 1H), 4.7 (m, 0.7H), 4.3 (m, 0.3H), 3.9 (s, 3H), 2.6–1.0 (m, 10H).

HRMS 316.1433 Calcd. for $C_{17}H_{20}N_2O_4$ 316.1450.

EXAMPLE 22

4-3-(Bicyclo[2.2.1]hept-2-yloxy)-4-Methoxyphenyl]-2,4-Imidazolidinedione

The 2,4-imidazolidinedione of Example 21 (3.0 g, 9.5 mmol) is dissolved in 40 ml THF and treated with 19 ml of a 1 molar solution of lithium aluminum hydride in THF. The reaction is refluxed for 48 hours, cooled and quenched with 10 ml saturated Na-K tartrate solution. The reaction is extracted 2×ethyl acetate, dried over $MgSO_4$, filtered, concentrated and flashed on $SiO_2$ with hexane/ethyl acetate (1:1) >20% EtOH/hexanes as the eluent. Obtained is 610 mg (21.2%) of the product as a crystalline solid. This material is 75l endo isomer.

MP=146°–148° C.

$^1$H NMR (300 MHz, CDCl$_3$): delta 6.8 (m, 3H), 5.2 (m, 2H), 4.8 (m, 1H), 4.6 (m, 0.7H), 4.2 (m, 0.3H), 3.9 (bs, 3H), 3.8 (m, 1H), 3.3 (m, 1H), 2.7–1.0 (m, 10H).

HRMS 302.1641 Calcd. for $C_{17}H_{22}N_2O_3$ 302.1630.

Analysis: Calcd.: C, 67.52; H, 7.34; N, 9.27. Found: C, 67.37; H, 7.30; N, 9.19.

EXAMPLE 23 alpha-N-Methylamine-3-(Endo-Tricyclo[3.3.1.1$^{3,7}$]dec-2-yloxy)-4-Methoxybenzene Acetonitrile The 2-adamantyl isovanillin ether of Preparation DD (5.29 g, 18.5 mmol) is dissolved in 150 ml of ethanol and is treated with sodium cyanide (1.36 g, 27.74 mmol) and methylamine hydrochloride (1.83 g, 27.74 mmol). To this is added 20 ml of water to homogenize the reaction mixture. The reaction is stirred for 48 hours at room temperature and is worked up by dilution with 300 ml ethyl ether and washing with 3×100 ml water. The organics are dried over $N_2SO_4$, filtered and concentrated in vacuo to yield 5.28 g (88%) of the aminonitrile as a viscous oil.

$^1$H NMR (300 MHz, CDCl$_3$): delta 7.0–6.75 (m, 3H), 4.6 (bs, 1H), 4.35 (bs, 1H), 3.8 (s, 3H), 2.5 (bs, 3H), 2.3–1.4 (m, 14H).

EXAMPLE 24

2-Methylamino-2-[3-(Endo-Tricyclo[3.3.1.1$^{3,7}$]dec-2-yloxy)-4-Methoxyphenyl]ethylamine The aminonitrile of Example 23 (5.95 g, 18.25 mmol) is dissolved in 200 ml of dry toluene and is added to a −78° C. solution of Dibal-H (91.25 mmol) in 270 ml of dry toluene. The reaction is stirred at −78° C. for 4 hours. The cooling bath is removed and the reaction is quenched slowly dropwise with 150 ml of a saturated sodium/potassium tartrate solution. The reaction is warmed slowly to room temperature and is diluted with 500 ml of ethyl acetate. The layers are separated and the aqueous is saturated with sodium chloride and extracted 1×100 ml methylene chloride. The collected organics are washed with 1×100 ml saturated sodium/potassium tartrate solution and 2×100 ml brine. The organics are dried over $K_2CO_3$ filtered and concentrated in vacuo to yield 6.0 g (~100%) of the adamantyl isovanillin diamine as a clear viscous oil.

$^1$H NMR (300 MHz, CDCl$_3$): delta 6.9–6.7 (m, 3H), 4.4 (bs, 1H), 3.85 (s, 3H), 3.35 (m, 1H), 2.8 (m, 2H), 2.3 (s, 3H), 2.2–1.4 (m, 14H).

EXAMPLE 25

1-Methyl-5-[3-(Endo-Tricyclo[3.3.1.1$^{3,7}$]dec-2-yloxy)-4-Methoxyphenyl-2-Imidazolidinone The diamine of Example 24 (6.0 g, 18.2 mmol) is dissolved in 180 ml of tetrahydrofuran and is treated with N,N-carbonyldiimidazole and is stirred at room temperature for 24 hours. The reaction mixture is diluted with 250 ml of ethyl ether and 200 ml of water. The organics are washed with 1×100 ml 0.8N NaOH solution, 1×100 ml 0.5N HCl solution, 1×water, dried over $Na_2SO_4$, filtered and concentrated in vacuo. The residue is chromatographed on $SiO_2$ with 50% ethyl acetate/hexanes as the eluent. The appropriate fractions are collected and concentrated in vacuo to yield 1.85 g (28%) of the adamantyl imidazolidinone as a white crystalline solid. MP=180.5°–181° C.

$^1$H NMR (300 MHz, CDCl$_3$): delta 6.8 (bs, 2H), 5.4 (bs, 1H), 4.45 (m, 2H), 3.82 (s, 3H), 3.66 (m, 1H), 3.18 (m, 1H), 2.57 (s, 3H), 2.4–1.5 (m, 14H).

HRMS 356.2115 (M+) calcd. for $C_{21}H_{28}N_2O_3$ 356.2100.

EXAMPLE 26 alpha-N-Ethylamino-3-(Bicyclo[2.2.1]hept-2-yloxy)-4-Methoxybenzene Acetonitrile

The 3-(bicyclo[2.2.1]hept-2-yloxy)-4-methoxybenzaldehydes of Example 1 (2.3 g, 9.35 mmol) are dissolved in 60 ml of ethanol and are treated with sodium cyanide (0.60 g, 12.2 mmol) and ethyl amine hydrochloride (1.0 g, 12.2 mmol). The solution is made homogenous with 4 ml of water and is stirred for 48 hours at room temperature. The reaction mixture is diluted with 250 ml of ethyl ether and 20 ml of saturated NaHCO$_3$ solution. The organics are washed with 3×100 ml water, 3×100 ml brine, dried with $Na_2SO_4$, filtered and concentrated in vacuo to yield 2.3 g (82%) of the ethyl aminonitrile as a viscous yellow oil. This material represents a 7:3 mixture of endo/exo isomers at the bicycloalkyl ether linkage.

$^1$H NMR (300 MHz, CDCl$_3$): delta 6.9–6.7 (m, 3H), 4.6 (bs, 1H), 4.55 (m, 7H), 4.1 (m, 3H), 3.7 (s, 3H), 2.8–1.0 (m, 15H).

EXAMPLE 27

2-Ethylamino-2-[3-(Bicyclo[2.2.1]hept-2-yloxy)-4-Methoxyphenyl]ethylamine

The ethylamino nitrile of Example 26 (2.3 g, 7.7 mmol) is dissolved in 70 ml of dry toluene and is added to a −78° C. solution of Dibal-H (38.5 mmol) in 100 ml toluene. The reaction is stirred for 2 hours at 78° C. and is warmed slowly to −40° C. where it is quenched slowly with 60 ml of a saturated sodium potassium tartrate solution. The reaction is then warmed to room temperature and is diluted with 200 ml of ethyl ether. The layers are separated and the aqueous is re-extracted with 100 ml ethyl acetate. The collected organics are washed with 3×Na K tartrate solution, 2×100 ml water, 3×100 ml brine, dried over $Na_2SO_4$, filtered and concentrated in vacuo to yield 1.9 g (81.2%) of the diamine as a brown oil. This material represents a 7:3 endo/exo mixture of isomers at the bicycloalkyl ether linkage.

$^1$H NMR (300 MHz, $CDCl_3$): delta 6.85–6.7 (m, 3H), 4.6 (m, 0.7H), 4.2 (m, 0.3H), 3.8 (bs, 3H), 3.65 (bs, 1H), 3.5 (m, 1H), 2.8 (m, 2H), 2.7–1.0 (m, 15H).

EXAMPLE 28

1-Ethyl-5-[3-(Bicyclo[2.2.1]hept-2-yloxy)-4-Methoxyphenyl]-2-Imidazolidinone

The ethyl-diamine of Example 27 (1.8 g, 5.9 mmol) is dissolved in 20 ml of dry tetrahydrofuran, is treated with N,N-carbonyldiimidazole (1.4 g, 8.8 mmol) and is stirred at room temperature for 24 hours. The reaction mixture is diluted with 100 ml of water and extracted 2×100 ml ethyl acetate. The collected organics are washed 2×50 ml 0.5 normal NaOH solution, 2×50 ml 0.5 normal HCl solution, 1×50 ml water and 2×50 ml brine. The organics are dried over $Na_2SO_4$ filtered and concentrated in vacuo. The resulting oil is titerated with ether, washed with ether and dried in vacuo to yield 579 mg (29.7%) of the imidazolidinone as a white solid. This material represents a 7:3 endo/exo mixture of isomers at the bicycloalkyl ether linkage. MP=149°–153° C.

$^1$H NMR (300 MHz, $CDCl_3$): delta 6.8–6.7 (m, 3H), 5.4–5.1 (bs, 1H), 4.55 (m, 1.7H), 4.15 (m, 0.3H), 3.8 (s, 2.1H), 3.77 (s, 0.7H), 3.6 (m, 1H), 3.4 (m, 1H), 3.2 (m, 1H), 2.72 (m, 1H), 2.54 (m, 0.7H), 2.45 (m, 0.3H), 2.27 (m, 0.3H), 2.23 (m, 0.7H), 2.0 (m, 2H), 1.8–1.1 (m, 6H), 0.98 (bt, 3H, J=7 Hz).

HRMS 330.1951(+) calcd. for $C_{19}H_{26}N_2O_3$ 330.1943.

EXAMPLE 29 alpha-N-Allylamino-3-(Bicyclo[2.2.1]hept-2-yloxy)-4-Methoxybenzene Acetonitrile

The 3-(bicyclo[2.2.1]hept-2-yloxy)-4-methoxybenzaldehydes of Example 1 (2.3 g, 9.35 mmol) are dissolved in 60 ml of ethanol and treated with sodium cyanide (0.60 g, 12.2 mmol), allyl amine (0.9 ml, 12.2 mmol) and 1.02 ml of concentrated HCl solution. The reaction mixture is stirred for 48 hours at room temperature. The reaction is diluted with 250 ml ethyl ether and 20 ml of saturated $NaHCO_3$ solution. The organics are washed with 3×100 ml water, 3×100 ml brine, dried over sodium sulfate, filtered and concentrated in vacuo to yield 2.7 g (92%) of the allyl cyanoamine as a viscous yellow oil. This material represents a 7:3 endo/exo mixture of isomers at the bicycloalkyl ether linkage.

$^1$H NMR (300 MHz, $CDCl_3$): delta 6.9–6.6 (m, 3H), 5.75 (m, 1H), 5.18 (bd, 1H, J=15 Hz), 5.07 (bd, 1H, J=9 Hz), 4.6 (bs, 1H), 4.5 (m, 0.7H), 4.07 (m, 0.3H), 3.7 (s, 3H), 3.4–3.2 (m, 2H), 2.6–1.0 (m, 10H).

EXAMPLE 30

2-Allylamino-2-[3-Bicyclo[2.2.1]hept-2-yloxy)-4-Methoxyphenyl]ethylamine

The allyl aminonitrile mixture of Example 29 (2.7 g, 8.6 mmol) is dissolved in 80 ml of dry toluene and is added dropwise to a −78° C. solution of Dibal-H (43 mmol) in 110 ml of dry toluene. The reaction is stirred to 2 hours at −78° C. and is warmed slowly to −40° C. where it is quenched slowly with 70 ml of saturated sodium potassium tartrate solution. The reaction is then warmed to room temperature and is diluted with 250 ml ethyl ether. The layers are separated and the aqueous is re-extracted with 150 ml ethyl acetate. The collected organics are washed with 3×50 ml Na K tartrate solution, 2×100 ml water, 3×100 ml brine, dried over $Na_2SO_4$, filtered and concentrated in vacuo to yield 2.4 g (88.3%) of the allyl diamine as a viscous pale brown oil. This material represents a 7:3 endo/exo mixture of isomer at the bicycloalkyl ether linkage.

$^1$H NMR (300 MHz, $CDCl_3$): delta 6.85–6.7 (m, 3H), 9.8 (m, 1H), 5.08 (bd, J=15 Hz), 5.01 (bd, J=9 Hz), 3.73 (s, 3H), 3.5 (m, 1H), 3.1 (m, 2H), 2.75 (m, 2H), 2.6–1.0 (m, 10H).

EXAMPLE 31

1-Allyl-5-[3-(Bicyclo[2.2.1]hept-2-yloxy)-4-Methoxyphenyl]-2-Imidazolidinone

The allyldiamine mixture of Example 30 (2.3 g, 7.3 mmol) is dissolved in 30 ml of dry tetrahydrofuran, is treated with N,N-carbonyldiimidazole, and is stirred at room temperature for 24 hours. The reaction mixture is diluted with 100 ml of water and extracted 2×100 ml ethyl acetate. The collected organics are washed 2×50 ml 0.5 normal NaOH solution, 2×50 ml. 5 normal HCl solution, 1×50 ml water, and 2×50 ml brine. The organics are dried over $Na_2SO_4$ filtered and concentrated in vacuo. The resulting oil is tierated with ether, washed with ether and dried in vacuo to yield 739 mg (29.6%) of the allyl imidazolidinone as a white solid. This material represents a 7:3 endo/exo mixture of isomers at the bicycloalkyl ether linkage. MP=110°–113° C.

$^1$H NMR (300 MHz, $CDCl_3$): delta 6.8–6.65 (m, 3H), 5.6 (m, 1H), 5.06 (bd, 1H, J=9 Hz), 4.98 (bd, 1H), J=15 Hz), 4.6 (m, 1.7H), 4.1 (m, 1.3H), 3.8 (s, 3H), 3.7 (m, 1H), 3.28 (m, 1H), 3.1 (dd, 1H, J=12 Hz, H=8 Hz), 2.57 (m, 0.7H), 2.48 (m, 0.3H), 2.3–2.2 (m, 1H, 2.1–1.1 (m, 8H).

HRMS 342.1971(+) Calcd. for $C_{20}H_{26}N_2O_3$ 342.1943.

EXAMPLE 32 alpha-N-Phenylethylamino-3-(Bicyclo[2.2.1]hept-2-yloxy)-4-Methoxybenzene Acetonitrile The norbornyl isovanillin aldehyde (2.3 g, 9.35 mmol) is dissolved in 60 ml of ethanol and is treated with sodium cyanide (0.60 g, 12.2 mmol), phenethylamine (1.5 ml, 12.2 mmol), and 1.02 ml of concentrated hydrochloric acid solution. The reaction is diluted with 250 ml of ethyl ether and 20 ml of saturated $NaHCO_3$ solution. The organics are washed with 3×100 ml water, 3×100 ml brine, dried over sodium sulfate, filtered and concentrated in vacuo to yield 3.6 g (~100%) of the phenethylaminonitrile as viscous yellow oil. This material represents a 7:3 mixture of isomers at the bicyclo[2.2.1]hept-2-yl ether linkage.

$^1$H NMR 300 MHz, CDCl$_3$): delta 7.4–7.1 (m, 5H), 6.9–6.7 (m, 3H), 4.65 (bs, 1H), 4.55 (m, 0.7H), 4.1 (m, 0.3H), 3.78 (bs, 3H), 3.1–2.5 (m, 5H), 2.3–1.0 (m, 9H).

EXAMPLE 33

2-Phenylethylamino-2-3-(Bicyclo[2.2.1]hept-2-yloxy)-4-Methoxyphenyl]ethylamine

The phenethylaminonitrile mixture of Example 32 (3.6 g, 9.4 mmol) is dissolved in 90 ml of dry toluene and is added dropwise to a −78° C. solution of diisobutylaluminumhydride (47 mmol) in 120 ml of dry toluene. The reaction is stirred for 2 hours at −78° C. and is warmed slowly to −40° C. where it is quenched slowly with 70 ml of saturated sodium potassium tartrate solution. The reaction is then warmed to room temperature and diluted with 250 ml ethyl ether. The layers are separated and the aqueous is re-extracted with 200 ml ethyl acetate. The collected organics are washed with 3×50 ml Na K tartrate solution, 2×100 ml water, 3×100 ml brine, dried over Na$_2$SO$_4$, filtered and concentrated in vacuo to yield 3.4 g (95%) of the phenethyldiamine as a pale brown viscous oil. This material represents a 7:3 endo/exo mixture of isomers at the bicycloalkyl ether linkage.

$^1$H NMR (300 MHz, CDCl$_3$): delta 7.4–7.1 (m, 5H), 6.9–6.7 (m, 3H), 4.6 (m, 0.7H), 4.2 (m, 0.3H), 3.8 (bs, 3H), 3.7 (bs, 1H), 3.55 (m, 1H), 3.1–2.5 (m, 7H), 2.5–1.0 (m, 9H).

EXAMPLE 34

1-Phenylethyl-5-[3-(Bicyclo[2.2.1]hept-2-yloxy)-4-Methoxyphenyl]-2-Imidazolidinone The phenethyldiamine endo/exo mixture of Example 33 (3.3 g, 8.7 mmol) is dissolved in 40 ml of dry tetrahydrofuran, treated with N,N'-carbonyldiimidazole, and is stirred at room temperature for 24 hours. The reaction mixture is diluted with 100 ml of water and extracted 2×100 ethyl acetate. The collected organics are washed 2×50 ml 0.5 normal NaOH solution, 2×50 ml 0.5 normal HCl solution, 1×50 ml water and 2×5 ml brine. The organics are dried over Na$_2$SO$_4$, filtered and concentrated in vacuo. The residue is flash chromatographed (32–60 SiO$_2$ 50% ethyl acetate/hexane→100% ethyl acetate). The appropriate fractions are concentrated in vacuo and tirerated with ether to yield 337 mg (10.6%) of the phenethylimidazolidinone as a white solid. This material represents a 7:3 endo/exo mixture of isomers at the bicycloalkyl ether linkage. MP=151°–154° C.

$^1$H NMR (300 MHz, CDCl$_3$): delta 7.4–7.1 (m, 5H), 6.9–6.7 (m, 3H), 4.9 (bs, 1H), 4.6 (m, 0.7H), 4.45 (m, 1H), 4.2 (m, 0.3H), 3.83 (bs, 3H), 3.7 (m, 2H), 3.26 (m, 1H), 3.1–2.5 (m, 4H), 2.4–1.1 (m, 9H).

HRMS 406. 2294 (M+) Calcd. for C$_{25}$H$_{30}$N$_2$O$_3$ 406.2257.

EXAMPLE 35

4-[3-(Endo-Bicyclo[2.2.1]hept-2-yloxy)-4-Methoxyphenyl]imidazole Hydrochloride

The 3-(Endo-bicyclo[2.2.1]hept-2-yloxy)-4-methoxyphenylglyoxal reactant (0.30 g, 1.03 mmol) and aqueous CH$_2$O 3 ml of a 37% aqueous solution) are dissolved in 3 ml of ethanol and to this is added 3 ml of concentrated NH$_4$OH. The reaction mixture is stirred for 1.5 hours at room temperature and is quenched with 20 ml water. The reaction mixture is extracted 2×ethyl acetate. The combined organics are mixed and adjusted to pH 2. The aqueous is separated and is basified to pH 9 with 50% NaOH. The aqueous is extracted 3×ethyl acetate. The organics are washed with water, dried over MgSO$_4$, filtered and concentrated in vacuo to yield 0.2 g of the imidazole as an oil. The oil is dissolved in 1 ml of acetone and is treated with 2 ml of HCl saturated acetone. The solution is treated with ether and the precipitate is collected to yield 0.12 g (68.4%) of the imidazole as its HCl salt. MP=201.202° C. (decomp).

$^1$H NMR (300 MHz, CDCl$_3$): delta 6.9–6.7 (m, 4H), 6.45 (m, 1H), 4.2 (m, 1H), 4.5 (s, 3H), 2.2 (m, 1H), 1.87 (m, 1H), 1.8–0.7 (m, 9H).

HRMS 284.1515(M+) Calcd. for C$_{17}$H$_{20}$N$_2$O$_3$ 284.1525.

EXAMPLE 36

3-(Indan-2-yloxy)-4-methoxybenzaldehyde (2.25 g, 839 mmol) is converted to the aminonitrile (2.36 g, 91.3%) according to the procedure of Example 2.

$^1$H NMR (300 MHz, CDCl$_3$): delta 7.3–7.05 (m, 6H), 6.85 (m, 1H), 5.2 (m, 1H), 4.7 (bs, 1H), 3.8 (s, 3H), 3.45 (dd, 2H, J=13 Hz, J=7 Hz), 3.25 (dd, 2H, J=13 Hz, J=3 Hz), 2.6 (s, 3H).

EXAMPLE 37

2-Methylamino-2-3-(Indan-2-yloxy)-4-Methoxyphenyl]ethylamine

The aminonitrile of Example 36 (2.25 g, 7.3 mmol) is reduced according to the procedure of Example 3 to produce the diamine (1.5 g, 65.5%) as a clear viscous oil.

$^1$H NMR (300 MHz, CDCl$_3$): delta 7.3–7.1 (m, 4H), 6.9 (m, 3H), 5.25 (m, 1H), 3.8 (s, 3H), 3.5 (m, 1H), 3.45 (dd, 2H, J=13 Hz, J=7 Hz), 3.25 (dd, 2H, J=13 Hz, J=3 Hz), 2.87 (m, 2H), 2.4 (bs, 3H).

EXAMPLE 38

1-Methyl-5-[3-(Indan-2-yloxy)-4-Methoxyphenyl]-2-Imidazolidinone

The diamine of Example 37 (1.50 g, 4.8 mmol) is converted to the imidazolidinone (126 mg, 37 mmol, 7.75%) according to the procedure of Example 4.

$^1$H NMR (300 MHz, CDCl$_3$): delta 7.3–7.2 (m, 4H), 6.9 (m, 3H), 5.3–5.2 (m, 1H), 5.0 (bs, 1H), 4.54 (m, 1H), 3.9 (s, 3H), 3.78 (m, 1H), 3.45 (dd, 2H, J=13 Hz, J=7 Hz), 3.3 (m, 1H), 3.25 (dd, 2H, J=13 Hz, J=3 Hz), 2.75 (s, 3H).

EXAMPLE 39 alpha-N-Methylamino-3-(Exo-Tricyclo[5.2.1.0$^{2.6}$]dec-8-yloxy-4-Methoxybenzene Acetonitrile The 3-exo-tricyclo[5.2.1.0$^{2.6}$]dec-8-yloxy)-4-methoxybenzaldehyde reactant (1.28 g, 4.47 mmol) is dissolved in 60 ml of ethanol and is treated with sodium cyanide (274 mg, 5.6 mmol) and methylamine hydrochloride (370 mg, 5.6 mmol). To this is added 20 ml of water to make the reaction homogeneous. The reaction is stirred for 20 hours at room temperature and is worked up by dilution with 250 ml of ether and is washed with 2×100 ml water, 1×100 ml pH 7 phosphate buffer, 1×100 ml brine, dried over Na$_2$SO$_4$, filtered and concentrated in vacuo to yield 1.13 g (78%) of the methylamino nitrile viscous oil.

¹H NMR (300 MHz, CDCl₃): delta 7.0–6.7 (m, 3H), 4.2 (m, 2H), 3.8 (s, 3H), 2.55 (s, 3H), 2.3–0.8 (m, 14H).

The following compound is prepared in like manner from the appropriate reactant:

alpha-N-methylamino-3-(endo-tricyclo[5.2.1.0$^{2,6}$]-dec-8-yloxy)-4-methoxybenzene acetonitrile in 89.4% yield:

¹H NMR (300 MHz, CDCl₃): delta 7.1–6.81 (m, 3H), 4.7 (bs, 1H), 4.6 (m, 1H), 3.9 (s, 3H), 2.6 (s, 3H), 2.8–1.0 (m, 14H).

EXAMPLE 40

2-Methylamino-2-[3-(Exo-Tricyclo[5.2.1.0$^{2,6}$]dec-8-yloxy)-4-Methoxyphenyl]ethylamine The title methylamino nitrile of Example 39 (1.94 g, 5.95 mmol) is dissolved in 60 ml of dry toluene and is added to a −78° C. solution of diisobutylaluminumhydride (29.75 mmol) as a solution in 150 ml of dry toluene. After the addition is complete the reaction is stirred for 4 hours at −78° C. and is then quenched with 65 ml of a saturated solution of sodium potassium tartrate. The reaction is warmed slowly room temperature and diluted with 500 ml of ethyl ether. The organic layer is separated and the remaining aqueous layer is saturated with NaCl and extracted with 2×100 ml ethylacetate. The collected organics are washed with 1×100 ml saturated Na K tartrate, 1×100 ml brine, dried over K₂CO₃, filtered and concentrated in vacuo to yield 1.8 g (92%) of the exo isomer of the diamine as a yellow viscous oil.

¹H NMR (300 MHz, CDCl₃): delta 6.85–6.65 (m, 3H), 4.15 (m, 1H), 3.75 (s, 3H), 3.38 m, 1H), 2.8 (m, 2H), 2.3 (s, 3H), 2.4–0.8 (m, 14H).

The endo-isomer is similarly prepared from the endo-methylamino nitrile isomer of Example 39:

¹H NMR (300 MHz, CDCl₃): delta 7.0–6.8 (m, 3H), 5.7 (m, 1H), 3.9 (s, 3H), 3.5 (m, 1H), 3.0–1.0 (m, 19H).

EXAMPLE 41

1-Methyl-5-[3-(Exo-Tricyclo[5.2.1.0$^{2,6}$]dec-8-yloxy)-4-Methoxyphenyl]-2-Imidazolidinone The title diamine of Example 40 (1.8 g, 5.45 mmol) is dissolved in 125 ml of tetrahydrofuran and is treated with N,N'-carbonyldiimidazole and is stirred at room temperature for 40 hours. The reaction is diluted with 300 ml of ether and washed with 2×100 ml water, 1×0.5 normal NaOH, 1×0.5 normal HCl, 1×100 ml water and 1×100 ml brine. The organics are dried over NaSO₄ and concentrated in vacuo. The residue is flashed on SiO₂ (32–64) with 50% ethyl acetate/hexanes as the eluent. The appropriate fractions are concentrated in vacuo to yield 625 mg (32%) of the imidazolidinone (endo isomer) as a white solid. MP=168°–170° C.

Analysis Calcd. for C₂₁H₂₈N₂O₃: C, 70.76; H, 7.92; N, 7.86. Found: C, 70.54; H, 7.92; N, 7.97.

¹H NMR (300 MHz, CDCl₃): delta 6.85–6.7 (m, 3H), 5.15 (bs, 1H), 4.4 (m, 1H), 4.12 (m, 1H, 3.81 (s, 3H), 3.68 (m, 1H), 3.22 (m, 1H), 2.6 (s, 3H), 2.3–0.8 (m, 14H).

HRMS 356.2155 (M+) Calcd. for C₂₁H₂₈N₂O₃ 356.2100.

The isomeric tricycloalkyl ether is prepared in like manner from the isomeric diamine of Example 40 in 20.7% yield:

MP=149°–152° C.

¹H NMR (300 MHz, CDCl₃): delta 6.9–6.8 (m, 3H), 5.15 (bs, 1H), 4.65 (m, 1H), 4.5 (m, 1H), 3.9 (s, 3H), 3.75 (m, 1H), 3.25 (m, 1H), 2.7 (s, 3H), 2.8–1.0 (m, 141H).

HRMS 356.2120 Calcd. for C₂₁H₂₈N₂O₃ 356.2099.

Analysis Calcd. for C₂₁H₂₈N₂O₃: C, 70.76; H, 7.92; N, 7.86. Found: C, 70.72; H, 7.86; N, 7.79.

EXAMPLE 42 alpha-N-Methylamino-3-(Endo-Tricyclo[5.2.1.0$^{2,6}$]dec-4-yloxy)-4-Methoxybenzene Acetonitrile The aminonitrile is prepared according to the procedure of Example 39 from the corresponding tricyclic isovanillin ether in 95.4% yield.

¹H NMR (300 MHz, CDCl₃): delta 7.0–6.7 (m, 3H), 4.7 (m, 1H), 4.65 (bs, 1H), 3.87, 3.85 (s, 0.3H), [2-methoxyls], 2.5 (bs, 3H), 2.2–8.5 (m, 14H).

EXAMPLE 43

2-Methylamino-2-[3-(Endo-Tricyclo[5.2.1.0$^{2,6}$]dec-4-yloxy)-4-Methoxyphenyl]ethylamine Following the procedure of Example 40, the diamine is prepared from the aminonitrile of Example 42.

¹H NMR (300 MHz, CDCl₃): delta 6.8–6.7 (m, 3H), 4.75 (m, 1H), 3.78 (s, 1H), 3.38 (m, 1H), 2.8 (m, 2H), 2.3 (s, 3H), 2.4–0.9 (m, 14H).

EXAMPLE 44

1-Methyl-5-[3-(Endo-Tricyclo[5.2.1.0$^{2,6}$]dec-4-yloxy)-4-methoxyphenyl]-2-Imidazolidinone The imidazolidinone is prepared according to the procedure of Example 41 from the diamine of Example 43 in 7.2% yield.

¹H NMR (300 MHz, CDCl₃): delta 6.8–6.7 (m, 3H), 5.75 (bs, 1H), 4.75 (m, 1H), 4.42 (m, 1H), 3.83 (s, 3H), 3.72 (m, 1H), 3.28 (m, 1H), 2.65 (s, 3H), 2.3–0.9 (m, 14H).

¹³C NMR (75.4 MHz, CDCl₃): delta 163.2, 150.8, 147.8, 131.8, 120.0, 114.5, 112.4, 82.5, 62.8, 56.2, 47.6, 46.2, 40.4, 37.7, 31.8, 28.8, 28.5 (17 lines).

Elemental Analysis: Found: C, 69.74, H, 7.93, N, 7.48 Calcd: C, 70.75, H, 7.91, N, 7.86

EXAMPLE 45 alpha-Formyl-[3-(Exo-Bicyclo[2.2.1]hept-2-yloxy)-4-Methoxyphenyl]Acetonitrile

The nitrile of Preparation R (1.2 g, 4.6 mmol) and ethylformate (2 ml) is dissolved in 10 ml benzene and to it is added portionwise sodium hydride [50% in oil] (0.39 g, 8.2 mmol). The reaction is warmed to 40° C. for 1.5 hours. The reaction mixture is cooled and diluted with 3 ml ethanol and 20 ml hexanes. The precipitate is collected, suspended in water and acidified with 1N HCl. The product is extracted 3×20 ml ethyl acetate and the ethyl acetate extracts are washed with brine, filtered and concentrated in vacuo to yield 0.62 g (47%) of the formyl compound as a thick yellow oil.

¹H NMR (300 MHz, CDCl₃): delta 7.4–6.7 (m, 4H), 4.25 (m, 1H), 4.25 (m, 1H), 3.8 (s, 3H), 2.6–1.0 (m, 10H).

In like manner, the following alpha-formyl cyanides are prepared from appropriate precursor benzyl cyanide derivatives: alpha-formyl-[3-(bicyclo[2.2.1]hept-2-yloxy)-4-methoxyphenyl]acetonitrile in 68.2% yield as a 7:3 mixture of endo:exo isomers.

¹H NMR (300 MHz, CDCl₃+CD₃OH): delta 7.2–7.0 (m, 2H), 6.65 (m, 2H), 4.5 (m, 0.7H), 4.1 (m, 0.3H), 3.7 (bs, 3H), 2.6–1.0 (m, 10H);

alpha-formyl-[3-(indan-2-yloxy)-4-methoxyphenyl]acetonitrile in 60% yield:

¹H NMR (300 MHz, CDCl₃): delta 7.8 (m, 1H), 7.3 (m, 1H), 7.2–7.1 (m, 4H), 6.9 (m, 3H), 5.15 (m, 1H), 3.8+3.77 (s, 3H), 3.4–3.1 (m, 4H);

alpha-formyl-[3-(endo-bicyclo[2.2.1]hept-2-yloxy)-4-methoxyphenyl]acetonitrile in 71.8% yield:

¹H NMR (300 MHz, CDCl₃): delta 7.3–7.1 (m, 2H), 6.8 (m, 3H), 4.6 (m, 1H), 3.9 (s, 3H), 2.6–1.0 (m, 10H).

EXAMPLE 46 alpha-Aminomethylene-[3-(Exo-Bicyclo[2.2.1]hept-2-yloxy)-4-Methoxyphenyl]Acetaldehyde Water washed Raney-Nickel excess is added to a solution of the title formyl compound of Example 45 (0.53 g, 1.81 mol) in 20 ml of ethanol. The reaction mixture is hydrogenated with 40 psi for 7 hours and is filtered through Celite which is subsequently washed with ethanol. The filtrate is concentrated in vacuo to yield 47 g (89.9%) of the imine aldehyde as an oil. This material exists as a mixture of iminealdehyde and enaminoaldehyde.

¹H NMR (300 MHz, CDCl₃): delta 9.6 (d, J=4 Hz) +9.1 (bs) (1H), 7.2–6.6 (m, 4H), 5.1 (bs, 1H), 4.2 (m, 1H), 3.85 (s, 3H), 2.6–1.0 (m, 10H).

The following compounds are similarly prepared from appropriate reactants as tautomeric mixtures:

an approximately 7:3 mixture of endo/exo isomers of alpha-aminomethylene-[3-(endo-bicyclo[2.2.1]hept-2-yloxy)-4-methoxyphenyl acetaldehyde in 83.3% yield;

alpha-aminomethylene-[3-(endo-bicyclo[2.2.1]hept-2-yloxy)-4-methoxyphenyl]acetaldehyde in 84% yield:

¹H NMR (300 MHz, CDCl₃): delta 9.5+9.0 (bs, 1H), 6.9 (m, 3H), 5.4 (bs, 1H), 4.6 (m, 1H), 3.8 (s, 3H), 2.6–1.0 (m, 10H);

alpha-aminomethylene-[3-(indan-2-yloxy)-4-methoxyphenyl]acetaldehyde in 84.6% yield:

¹H NMR (300 MHz, CDCl₃): delta 9.5+9.0 (bs, 1H), 7.2–7.1 (m, 4H), 6.9 (m, 3H), 5.3 (bs, 1H), 5.1 (bs, 1H), 3.8 (s, 3H), 3.1 (m, 4H).

EXAMPLE 47

5-[3-(Exo-Bicyclo[2.2.1]hept-2-yloxy)-4-Methoxyphenyl]-2-Pyrimidinone

The iminealdehyde of Example 46 (0.47 g, 1.63 mmol) is dissolved in 5 ml ethanol and is treated with 1 ml concentrated HCl and urea (0.12 g, 1.95 mmol). The reaction is warmed to reflux for 1.5 hours. The reaction mixture is cooled to room temperature, neutralized with aqueous NH₄OH and extracted 6×10 ml ethyl acetate. The combined organics are dried over MgSO₄, filtered and concentrated to dryness to afford 0.2 g (39.3%) of the pyrimidinone as a crystalline product. MP=195°–196° C.

¹H NMR (300 MHz, CDCl₃): delta 8.4 (m, 2H), 6.9–6.7 (m, 4H), 4.2 (m, 1H), 3.82 (s, 3H), 2.5–0.9 (m, 10H).

HRMS 312.1472 (+) Calcd. for C₁₈H₂₀N₂O₃ 312.1474.

Similarly the following compounds are prepared from the appropriate precursor enamino aldehydes:

5-[3-(bicyclo[2.2.1]hept-2-yloxy)-4-methoxyphenyl]-2-pyrimidone in 60.3% yield as a 7:3 endo/exo isomeric mixture.

¹H NMR (300 MHz, CDCl₃): delta 8.4 (m, 2H), 6.9–6.7 (m, 4H), 4.65 (m, 0.7H), 4.25 (m, 0.3H), 3.85 (bs, 3H), 2.7–1.1 (m, 10H);

5-[3-(indan-2-yloxy)-4-methoxyphenyl]-1,2-dihydropyrimidinone in 13.9% yield:

¹H NMR (300 MHz, CDCl₃): delta 8.6 (bs, 2H), 7.3–7.0 (m, 7H), 5.35 (m, 1H), 3.75 (s, 3H), 3.4–3.0 (m, 4H);

5-[3-(endo-bicyclo[2.2.1]hept-2-yloxy)-4-methoxyphenyl]-1,2-dihydropyrimidinone in 47% yield:

MP 220° C.

¹H NMR (300 MHz, CDCl₃): delta 8.5 (bs, 2H), 7.21 (s, 1H), 6.9–6.8 (m, 3H), 4.6 (m, 1H), 3.85 (s, 3H), 2.6–1.0 (m, 10H).

EXAMPLE 48 alpha-N-Methylamino-4-Methoxy-3-Nitrobenzene Acetonitrile

The aminonitrile is prepared according to the procedure of Example 39 from 4-methoxy-2-nitrobenzaldehyde (25.80 g, 142.4 mmol). The product is isolated by filtration to yield 31.20 g (99%) of product.

¹H NMR (90 MHz, CDCl₃): delta 7.8–7.2 (m, 3H), 5.0 (bs, 1H).

EXAMPLE 49

2-Methylamino-2-(4-Methoxy-3-Nitrophenyl)ethylamine

The aminonitrile of Example 48 (15 g, 67.81 mmol) is dissolved in ]50 ml of toluene and is cooled to −78° C. To it is added Dibal-H (181 ml, 27.1.2 mmol) as a 1.5 molar solution in toluene. The reaction is stirred at −78° C. for 3 hours, warmed to 0° C. and quenched with 150 ml water. The pH is adjusted to 2 with 6 normal HCl and is washed with 2×50 ml ether.

The aqueous is pH adjusted to 12 with 25% NaOH solution and is extracted 3×100 ml methylene chloride, dried over MgSO₄, filtered and concentrated in vacuo to yield 11.0 g (72%) of the nitrodiamine as a dark brown oil. This material is used with no further purification.

EXAMPLE 50

1-Methyl-5-4-Methoxy-3-Nitrophenyl)-2-Imidazolidinone

The nitroimidazolidinone is prepared by the procedure of Example 40 from the nitrodiamine of Example 49 (11 g, 48.88 mmol) to yield 4.51 g (37%) of the product as a light orange solid.

¹H NMR (90 MHz, CDCl₃): delta 7.7–7.0 (m, 3H), 4.5 (m, 1H), 3.9 (s, 3H), 3.7 (m, 1H), 3.2 (m, 1H), 2.6 (s, 3H).

EXAMPLE 51

1-Methyl-5-(3-Amino-4-Methoxyphenyl)-2-Imidazolidinone

Platinum oxide (0.135 g) is suspended in 1 ml concentrated hydrochloric acid. To this is added to nitroimidazolidinone of Example 50 (4.51 g, 17.95 mmol) as a solution in 30 ml methanol. The volume of the reaction is brought to 200 ml with methanol and is placed on a Parr shaker with 50 psi H₂ pressure for 45 minutes. The catalyst is filtered off and the reaction is concentrated in vacuo to yield an oil which is redissolved in ethyl acetate, washed with 1 normal NaOH solution, dried over MgSO₄, filtered and concentrated in vacuo to yield the crude aniline as an oil which is carried on with no further purification.

¹H NMR (300 MHz, CDCl₃): delta 6.7 (m, 3H), 5.6 (bs, 1H), 4.4 (m, 1H), 3.8 (s, 3H), 3.7 (m, 1H), 3.2 (m, 1H), 2.6 (s, 3H).

EXAMPLE 52

1-Methyl-5-[3-(Bicyclo[2.2.1]hept-2-ylamino)-4-Methoxyphenyl]-2-Imidazolidinone

The aniline of Example 51 (3.07 g, 17.95 mmol) is dissolved in 60 ml of glacial acetic acid and to this is added norcamphor 2.37 g, 21.54 mmol). The reaction is cooled to 5° C. and to it is added sodium, cyanoborohydride (1.36 g, 21.54 mmol). The reaction is poured onto ice and is pH adjusted to 7 with 1 normal NaOH solution. The aqueous is extracted with methylene chloride dried over MgSO₄, filtered and concentrated vacuo to afford a brown oil which is flashed on SiO₂ with ethyl acetate as the eluent. The appropriate fractions are combined and concentrated in vacuo to yield a white paste which is tritarted with ether to yield (0.57 g 10%) of the product as a white crystalline solid. MP=171°–174° C.

¹H NMR (250 MHz, CDCl₃): delta 6.75–6.5 (m, 3H), 4.6 (m, 1H), 4.4 (m, 1H), 3.86 (s, 3H), 3.7 (m, 1H), 3.25 (m, 1H), 2.65 (s, 3H), 2.6–2.0 (m, 3H), 1.8–1.2 (m, 6H), 0.85 (m, 1H).

Elemental Analysis: Found: C, 68.98, H, 7.40, N, 13.41 Calcd: C, 68.03, H, 7.99, N, 13.37

HRMS 315.1948 (M+) Calcd for $C_{18}H_{23}N_3O_2$ 315.1946.

EXAMPLE 53

4-[3-(Bicyclo[2.2.1]hept-2-yloxy)-4-Methoxyphenyl]-pyrazole

The appropriate enamino-aldehyde of Example 46 (0.20 g, 0.697 mM) is dissolved in 5 ml ethanol and treated with 0.2 ml hydrazinc. The reaction mixture is refluxed for 30 minutes, cooled and quenched with water. The product is extracted 2×ethyl acetate and the combined organics are washed, dried over MgSO₄, filtered and concentrated in vacuo to yield a yellow oil. The crude material is crystallized from ethyl acetate to yield 0.11 g (55.3%) of the pyrazole as a white crystalline solid. This material represents an 7.3 endo to exo mixture at the norbornyl ether linkage.

MP=180°–181° C.

¹H NMR (30 MHz, CDCl₃): delta 7.8 (bs, 2H), 7.1–6.84 (m, 3H), 4.7 (m, 0.7H), 4.3 (m, 0.3H), 3.86 (bs, 3H), 2.8–1.0 (m, 10H).

HRMS 284.1531 (M+) Calcd. for $C_{17}H_2N_2O_2$ 284.1525.

EXAMPLE 54

6-[3-(Bicyclo[2.2.1]hept-2-yloxy)-4-Methoxyphenyl-]imidazo[1,2-a]Pyrimidine

The title enamino-aldehyde of Example 46 (0.20 g, 0.7 mmol), 2-aminoimidazole sulfate (0.27 g, 1 mmol) are dissolved in ethanol, treated with 0.5 ml, concentrated HCl and refluxed for 1 hour. The reaction is cooled, quenched with water and extracted 3×ethyl acetate. The combined organics are washed with brine, dried over MgSO₄, filtered and concentrated in vacuo. The crude material is crystallized from ethyl acetate to yield 0.20 g (85.3%) of the compound as a beige crystalline solid. This material is 7.3 endo/exo mixture of bicycloalkyl isomers.

MP=130° C. (Dec.)

¹H NMR (300 MHz, CDCl₃): delta 8.8 (m, 1H), 8.5 (m, 1H), 7.85 (bs, 1H), 7.6 (bs, 1H), 7.2–6.9 (m, 3H), 4.75 (m, 7H), 4.3 (m, 13H), 3.9 (bs, 3H), 2.8–1.1 (m, 10H).

HRMS 335.1610 Calcd. for $C_{20}H_{21}O_2N_3$ 335.1633.

EXAMPLE 55

6-(3-Bicyclo[2.2.1]hept-2-yloxy)-4-Methoxyphenyl]-pyrazolo[2,3-a]Pyrimidine

The title enamino aldehyde of Example 46 (0.20 g, 0.7 mmol) and 3-aminopyrazole (83 mg, 1.0 mmol) are dissolved in 5 ml of ethanol and treated with 0.5 ml concentrated HCl. The reaction mixture is refluxed for 30 minutes, cooled to room temperature, quenched with water and the product is extracted 2×ethyl acetate. The combined organics are washed with brine, dried over MgSO₄, filtered and concentrated in vacuo. The crude material is crystallized from ethyl acetate/hexanes to produce 0.180 g (76.7%) of the product as a crystalline solid comprising endo/exo mixture at the bicycloalkyl residue.

MP=136°–137° C.

¹H NMR (300 MHz, CDCl₃): delta 8.9 (bs, 1H), 8.75 (m, 1H), 8.15 (m, 1H), 7.2–7.0 (m, 3H), 6.8 (m, 1H), 4.75 (m, 7H), 4.3 (m, 0.3H), 3.9 (bs, 3H), 2.8–1.1 (m, 10H).

EXAMPLE 56

Ethyl 3-[3-(Bicyclo[2.2.1]hept-2-yloxy)-4-Methoxyphenyl]-2-Carbethoxypropenoate

The aldehyde, 3-(bicyclo[2.2.1]hept-2-yloxy)-4-methoxybenzaldehyde (5.0 g, 0.02 mmole), diethyl malonate (3.21 g, 0.02 mol) and piperidine are dissolved in toluene and refluxed for 15 hours. The reaction is cooled, concentrated in vacuo and the resulting oil taken up in ethyl acetate. The organics are washed with saturated NH₄Cl solution, water, brine, dried, filtered and concentrated in vacuo to afford 6.56 g (84.5%) of diester product as a 7:3 endo/exo isomer mixture.

¹H NMR (300 MHz, CDCl₃): delta 7.6 (m, 1H, 7.2–16.7 (m, 3H), 4.5 (m, 0.7H), 4.4–4.1 (m, 5H), 3.85 (bs, 3H), 2.6–1.0 (m, 6H).

EXAMPLE 57

Ethyl 3-[3-(Bicyclo[2.2.1]hept-2-yloxy)-4-Methoxyphenyl]-3-Cyanopropanoate

The diester of Example 56 (6.5 g, 0.0167 mole) and sodium cyanide (0.833 g, 0.017 mole) are dissolved in 75 ml of ethanol and stirred at room temperature for 24 hours. The ethanol is removed in vacuo, the resulting solid is partitioned between ethyl acetate and water and the aqueous layer is reextracted with ethyl acetate. The combined organics are washed with water and brine, dried over MgSO₄, filtered and concentrated in vacuo to afford 4.45 g (77.8%) of the cyano ester as a yellow oil comprising a 7:3 mixture of endo/exo bicycloalkyl isomers.

¹H NMR (300 MHz, CDCl₃): delta 6.9–6.75 (m, 3H), 4.6 (m, 7H), 4.45 (m, 1H), 4.3 (q, 24, J=5 Hz), 4.2 (m, 3H), 4.1 (m, 2H), 3.85 (s, 3H), 2.8–1.1 (m, 3H).

EXAMPLE 58

4-[3-(Bicyclo[2.2.1]hept-2-yloxy)-4-Methoxyphenyl]-2-Pyrrolidone

Platinum oxide (400 mg) is suspended in 50 ml of acetic acid and is activated by hydrogenation at 50 psi for 1 hour. The cyanoester of Example 57 (2.0 g, 5.84 mmol) is added to the PtO₂ suspension as a solution in 50 ml of acetic acid. The reaction mixture is shaken under 50 psi H₂ for 18 hours. The reaction mixture is purged with N₂, concentrated in vacuo and the last traces of acetic acid are azeotroped with toluene in vacuo. The resulting oil is dissolved in 50 ml toluene, treated with 10 ml triethylamine and refluxed for 24 hours. The reaction mixture is then cooled, concentrated in vacuo and the residue dissolved in ethyl acetate. The organics are washed with 1N HCl, water, brine, dried over MgSO₄, filtered and concentrated in vacuo to afford as the alpha-carboethoxy lactam. This material is dissolved in ethanolic NaOH and refluxed until no ester remains by TLC. The reaction mixture is cooled, neutralized with 1N HCl and extracted 3×ethyl acetate. The organics are washed, dried, filtered and concentrated to afford the alpha-carboxylic acid which is thermally decarboxylated at 180° C. to afford 611 mg (34.7%) of the pyrrolidone as a white solid. This material is an 7:3 mixture of endo/exo bicycloalkyl isomers.

MP=153°-156° C.

$^1$H NMR (300 MHz, CDCl₃): delta 6.9-6.6 (m, 3H), 4.6 (m, 0.7H), 4.2 (m, 0.3H), 3.85 (bs, 3H), 3.8 (m, 1H), 3.62 (m, 1H), 3.4 (m, 1H), 2.7 (m, 1H), 2.6 (m, 1H), 2.5 (m, 1H), 2.3 (m, 1H), 2.1-1.0 (m, 8H).

EXAMPLE 59

3-[3-(Bicyclo[2.2.1]hept-2-yloxy)-4-Methoxyphenyl]-1-Dimethylamino-1-Propen-3-one 1-[3-(Bicyclo[2.2.1]hept-2-yloxy)-4-methoxyphenyl]ethanone (1.5 g, 5.84 mmol) is dissolved in 5 ml tris-dimethyl aminomethane and refluxed for 30 minutes. The reaction is cooled, quenched with water and the product extracted 3×ethyl acetate. The combined organics are washed with H₂O, brine, dried, filtered and concentrated in vacuo yield 1.4 g (77.3%) of the enamino-ketone product.

$^1$H NMR (60 MHz, CDCl₃): delta 7.7 (d, 1H, 12 Hz), 7.5-7.2 (m, 2H), 7.0-6.7 (m, 1H), 5.65 (d, 1H, 12 Hz), 4.8-4.1 (m, 1H), 3.95 (bs, 3H), 3.0 (s, 6H), 2.9-1.0 (m, 10H).

In like manner there is prepared from appropriate reactants: 3-[(3-indane-2-yloxy)-4-metoxyhenyl]-1-dimethylamino-1-propen-3-one in 71.8% field.

$^1$H NMR (60 MHz, CDCl₃): delta 7.8-6.6 (m, 8H), 6.7 (d, 1H, J=12 Hz), 3.8 (s, 3H), 3.3 (m, 4H), 2.8 (bs, 6H).

EXAMPLE 60

4-[3-(Bicyclo[2.2.1]hept-2-yloxy)-4-Methoxyphenyl]-4-Hydroxy-1,2,3,4-Tetrahydro-2-Pyrimidinone The enamino-ketone of Example 59 (0.9 g, 2.9 mmol) and urea (0.21 g, 3.5 mmol) are dissolved in 10 ml ethanol, treated with 4 ml 1N HCl and refluxed for 1 hour. The reaction is cooled, quenched with water and the product extracted 2×ethyl acetate. The combined organics are washed with brine, dried, filtered and concentrated in vacuo. The crude material is crystallized from CH₂Cl₂/hexanes to yield 0.55 g (57.5%) of the product as beige crystals. This material is 7:3 endo/exo mixture of isomers.

MP=167°-169° C. (Dec.)

$^1$H NMR (300 MHz, CDCl₃): delta 7.7-7.4 (m, 3H), 6.8 (m, 1H), 6.18 (m, 1H), 5.5 (b,2H), 4.7 (m, 0.7H), 4.3 (m, 0.3H), 3.95 (s, 3H), 2.8-1.2 (m, 10H).

HRMS 330.1614 Calcd. for C₁₈H₂₂N₂O₄ 330.1580.

EXAMPLE 61

4-[3-(Bicyclo[2.2.1]hept-2-yloxy)-4-Methoxyphenyl]1,2-Dihydro-2-Pyrimidinone

The hydroxypyrimidinone of Example 60 (0.2 g, 0.61 mmol) is dissolved in 5 ml ethanol, treated with 2.5 ml 1N HCl and refluxed for 6 hours. The reaction is cooled to room temperature, quenched with water and the product extracted 3×ethyl acetate. The organics are washed, dried, filtered and concentrated in vacuo to yield a crude substance which is crystallized from ethyl acetate to give 60 mg (31.5%) of the pyrimidinone as a crystalline solid. This material is a 7:3 mixture of endo/exo bicycloalkyl isomers.

MP=220° C.

$^1$H NMR (300 MHz, CDCl₃): 7.8-7.45 (m, 3H), 6.9 (m, 1H), 6.8 (m, 1H), 5.15 (m, 1H), 4.75 (m, 0.7H), 4.35 (m, 3H), 3.95 (bs, 3H), 2.8-1.2 (m, 10H).

HRMS 312.1520 Calcd. for C₁₈H₂₀N₂O₃ 312.1474.

EXAMPLE 62

5-[3-(Bicyclo[2.2.1]hept-2-yloxy)-4-Methoxyphenyl]imidazo[1,2-a]pyrimidine

The enamino-ketone of Example 59 (0.4 g, 1.27 mmol) and 2-aminoimidazole sulfate are dissolved in 5 ml ethanol, treated with 0.5 ml concentrated HCl and refluxed for 1.5 hours. The reaction is cooled, quenched with water, pH adjusted to 9 and the product extracted 2×ethyl acetate. The combined organics are washed, dried, concentrated in vacuo and the crude material crystallized from ether to provide 0.11 g (28.9%) of the product as a beige crystalline solid comprising 7.3: endo/exo mixture of isomers.

MP=140°-141° C.

$^1$H NMR (300 MHz, CDCl₃): delta 8.6 (d, 1H), 7.81 (bs, 1H), 7.74 (bs, 1H), 7.3-7.0 (m, 3H), 6.8 (m, 1H), 4.63 (m, 0.7H), 4.21 (m, 0.3H), 3.95 (bs, 3H), 2.7-1.1 (m, 10H).

HRMS 335.1631 Calcd. for C₂₀H₂₁N₂O₃ 335.1634.

EXAMPLE 63

7-3-(Bicyclo[2.2.1]hept-2-yl)-4-Methoxyphenyl]-Pyrazolo[2,3-a]Pyrimidine

The enamino ketone of Example 59 (0.40 g, 1.27 mmol) and 3-aminopyrazole (0.16 g, 1.9 mmol) are dissolved in ethanol, treated with 0.5 ml, concentrated HCl and refluxed for 1 hour. The reaction is cooled, quenched with water, pH adjusted to 9 and the product extracted 2×ethyl acetate. The combined organics are washed, dried, filtered, concentrated in vacuo and the crude material chromatographed on 150 mesh SiO₂ with ethyl acetate as the eluent. The free base is dissolved in ether and treated dropwise with concentrated HCl. The HCl salt is collected by filtration to yield 0.15 g (35.6%) of the 7:3 endo/exo isomers as a yellow crystalline solid.

MP=148°-149° C.

$^1$H NMR 300 MHz, CDCl₃): delta 8.5 (m, 1H), 8.16 (m, 1H), 7.7-7.6 (m, 2H), 7.1-7.0 (d, 1H, J=6 Hz), 6.9 (m, 1H), 6.75 (m, 1H), 4.7 (m, 0.7H), 4.35 (m, 0.3H), 3.85 (bs, 3H), 2.7-1.1 (m, 10H).

HRMS 335.1659 Calcd. for C₂₀H₂₁N₃O₂ 335.1633.

EXAMPLE 64

5-[3-(Bicyclo[2.2.1]hept-2-yloxy)-4-Methoxyphenyl]-1,2,3,4-Tetrahydro-2-Pyrimidinone alpha-aminomethylene-3-endo-(bicyclo[2.2.1]hept-2-yloxy)-4-methoxyphenyl]acetaldehyde of Example 46 (0.60 g, 2.08 mmol) and urea (0.20 g, 3.3 mmol) are dissolved in 10 ml ethanol, treated with 2 ml of concentrated HCl solution and refluxed for 1.5 hours. The reaction is cooled, neutralized with NH4OH solution and the product extracted 4×ethyl acetate. The organics are washed, dried, filtered, concentrated in vacuo and the resulting residue crystallized from ether to afford 0.38 g (58.6%) of 5-[3-(bicyclo[2.2.1]hept-2-yloxy)-4-methoxyphenyl]-1,2-dihydro-2-pyrimidinone, identical to the product described in Example 47.

The pyrimidinone (0.38 g, 1.22 mmol) is dissolved in 20 ml ethanol and treated with 0.5 g Raney Nickel, 40 psi hydrogen and refluxed for 18 hours. The reaction is cooled, filtered through celite, and the filtrate concentrated in vacuo. The residue is crystallized from ethyl acetate to afford 0.12 g (31.8%) of the dihydro pyrimidinone as a crystalline solid comprising a 7:3 mixture of endo/exo norbornyl isomers.

MP=136°–137° C.

$^1$H NMR (300 MHz, CDCl$_3$): delta 7.1 (bs, 1H), 6.9–6.7 (m, 3H), 6.4 (d, 1H, J=5 Hz), 5.4 (bs, 1H), 4.65 (m, 0.7H), 4.4 (bs, 2H), 4.25 (m, 0.3H), 3.85 (s, 3H), 2.7–1.2 (m, 10H).

HRMS 314.1644 (+) Calcd. for C$_{18}$H$_{22}$N$_2$O$_3$ 314.1630.

In like manner the exo isomer of the title compound is prepared in 60.3% yield from the exo isomer of 5-[3-(exo-bicyclo[2.2.1]hept-2-yloxy)-4-methoxyphenyl]-1,2-dihydro-2-pyrimidinone (Example 47) by hydrogenation as described above:

$^1$H NMR (300 MHz, CDCl$_3$+CD$_3$OD): delta 6.7 (m, 3H), 6.2 (bs, 1H), 4.15 (m, 1H), 3.78 (s, 3H), 3.3 (bs, 2H), 2.4–1.0 (m, 10H).

HRMS 314.1647 (M+) Calcd. for C$_{18}$H$_{22}$N$_2$O$_3$, 314.1625.

EXAMPLE 65

5-[3-(Bicyclo[2.2.1]hept-2-yloxy)-4-Methoxyphenyl]-hexahydro-2-Pyrimidinone

The tetrahydro pyrimidinone of Example 64 (0.30 g, 0.882 mmol) is dissolved in 15 ml methanol, treated with 0.3 g Raney Nickel and hydrogenated at 40 psi for 6 hours. The reaction is filtered through celite dried over MgSO$_4$, filtered, concentrated in vacuo and triturated from ether to provide 0.275 g (98%) of the cyclic urea as a crystalline solid. This material is a 7:3 mixture of endo/exo bicycloalkyl isomers.

MP=>220° C.

$^1$H NMR (300 MHz, CDCl$_3$): delta 6.85–6.6 (m, 3H), 5.1 (bs, 2H), 4.65 (m, 0.7H), 4.25 (m, 3H), 3.9 (bs, 3H), 3.5 (m, 4H), 3.1 (m, 1H), 2.7–1.1 (m, 10H).

MS 316 (M+)Calcd. 316.1787.

By means of this procedure there is prepared from appropriate reactants:

5-[3-(indan-2-yloxy)-4-methoxyphenyl]hexahydro-2-pyrimidinone in 75.6% yield:

MP=212°–214° C.

$^1$H NMR (300 MHz, DMSO): delta 7.2–6.8 (m, 7H), 6.3 (bs, 2H), 5.2 (m, 1H), 3.7 (s, 3H), 3.4–3.2 (m, 7H), 3.0 (m, 2H).

$^{13}$C NMR (75.43 MHz, DMSO): delta 156.0, 148.4, 146.8, 140.8, 132.9, 126.4, 124.6, 119.5, 113.9, 112.2, 79.2, 77.9, 55.4, 45.5, 36.9.

HRMS 338.1629 (M+) Calcd. for C$_{20}$H$_{22}$N$_2$O$_3$, 338.1630.

5-[3-(endo-bicyclo[2.2.1]hept-2-yloxy)-4-methoxyphenyl]hexahydro-2-pyrimidinone in 66.5% yield:

$^1$H NMR (300 MHz, CDCl$_3$): 7.2 (bs, 2H), 6.8–6.7 (m, 3H), 4.6 (m, 1H), 3.8 (s, 3H), 3.4 (m, 4H), 3.15 (m, 1H), 2.6–1.0 (m, 10H).

5-[3-(exo-bicyclo[2.2.1]hept-2-yloxy)-4-methoxyphenyl]hexahydro-2-pyrimidinone in 82% yield:

$^1$H NMR 300 MHz, CDCl$_3$): delta 6.8–6.7 (m, 3H), 5.4 (bs, 2H), 4.15 (m, 1H), 3.8 (s, 3H), 3.4 (m, 4H), 3.15 (m, 1H), 2.4–1.0 (m, 10H).

HRMS 316.1801 (M+) Calcd. for C$_{18}$H$_{24}$N$_2$O$_3$, 316.1757.

EXAMPLE 66

4-[3-(Indan-2-yloxy)-4-Methoxyphenyl]-4-Hydroxy-1,2,3,4-Tetrahydro-2-Pyrimidinone and 4-[3-(Indan-2-yloxy)-4-Methoxyphenyl]1,2-Dihydro-2-Pyrimidinone The indanyl substituted enamino-ketone of Example 59 (10.5 g, 4.45 mmol) and urea (0.4 g, 6.68 mmol) are dissolved in 10 ml ethanol and 5 ml 1N HCl and refluxed for 2 hours. The reaction mixture is cooled, quenched with H$_2$O and neutralized with saturated NaHCO$_3$ solution. The product is extracted 3×ethyl acetate and the combined organics are washed with brine, dried over MgSO$_4$, filtered and concentrated in vacuo to provide a crude mixture of two products which are separated by SiO$_2$ chromatography with ethyl acetate/hexanes as the eluent. Obtained is 0.15 g (9%) of 0.15 g (10%) of crystalline materials.

The 4-hydroxy-1,2,3,4-tetrahydropyrimidinone product. MP=207°–208° C.

$^1$H NMR (300 MHz, CDCl$_3$/CD$_3$OD): delta 7.7–7.5 (m, 3H), 7.25–7.1 (m, 4H), 6.91 (d, 1H, J=6 Hz), 5.3 (m, 1H), 3.9 (s, 3H), 3.45 (dd, 2H, J=5 Hz), 3.3 (dd, 2H, J=12 Hz, J=3 Hz).

HRMS 352.1454 Calcd. for C$_{20}$H$_2$N$_2$O$_4$ 352.1423.

The 1,2-dihydropyrimidinone product.

MP=>220° C.

$^1$H NMR (300 MHz, DMSO): delta 8.1 (m, 1H), 7.85 (m, 2H), 7.4–7.0 (m, 6H), 5.5 (m, 1H), 3.95 (s, 3H), 3.5 (m, 3H), 3.25 (bd, 2H, J=12 Hz).

HRMS 334.1332 Calcd. for C$_{20}$H$_{18}$N$_2$O$_3$ 334.1318.

EXAMPLE 67

4-[3-(Indan-2-yloxy)-4-Methoxyphenyl]-1,2-Dihydro-2-Pyrimidinone

The indanyl substituted enamino-ketone of Example 59 (800 mg, 2.4 mmol) and urea (210 mg, 3.56 mmol) are dissolved in 5 ml of 1N HCl and 15 ml ethanol and refluxed for 4 hours. The reaction is cooled, quenched with H$_2$O and the product is extracted 3×ethyl acetate. The organics are washed, dried and concentrated. The crude product is crystallized from ethyl acetate to provide 0.32 g (40%) as a beige crystalline solid.

This material is identical in all respects to the product described in Example 66.

EXAMPLE 68

4-[3-(Indan-2-yloxy)-4-Methxoyphenyl]hexahydro-2-Pyrimidinone

The pyrimidinone of Example 67 (0.32 g, 0.96 mmol) is dissolved in 15 ml of methanol, treated with Raney Nickel and hydrogenated under 40 psi for 8 hours at room temperature. The mixture is filtered through Celite and the catalyst washed several times with methanol. The organics are concentrated in vacuo and the crude residue triturated from ether to provide 20 mg (58%) of the product as a crystalline solid.

MP=182°-183° C.

$^1$H NMR (300 MHz, CDCl$_3$): delta 7.4–6.8 (m, 7H), 5.55 (bs, 1H), 5.25 (m, 1H), 5.2 (bs, 1H), 4.6 (m, 1H), 3.9 (s, 3H), 3.6–3.2 (m, 6H), 2.2 (m, 1H), 2.0 (m, 1H).

HRMS 338.1665 Calcd. for C$_{20}$H$_{22}$N$_2$O$_3$ 338.1631.

EXAMPLE 69

5-[3-(Indan-2-yloxy)-4-Methoxyphenyl]-1,2,3,4-Tetrahydro-2-Pyrimidinone

5-[3-(Indan-2-yloxy)-4-methoxyphenyl]-1,2-dihydro-2-pyrimidinone (740 mg, 2.2 mmol) is dissolved in 10 ml. acetic acid cooled in an ice bath and treated with NaCNBH$_3$ (140 mg, 2.2 mmol). The reaction is stirred for hours and is worked up by dilution with water and extraction with ethyl acetate. The collected organics are washed with water, brine, dried over Na$_2$SO$_4$, filtered and concentrated in vacuo to afford 640 mg (87.4%) of the title product as a white crystalline solid.

MP=198°-201° C.

$^1$H NMR (300 MHz, CDCl$_3$): delta 7.5 (bs, 1H), 7.2 (m, 4H), 6.85 (m, 3H), 6.38 (bd, 1H), 5.9 (bs, 1H, 4.3 (bs, 2H), 3.8 (s, 3H), 3.4–3.1 (m, 4H).

Similarly, 5-[3-(endo-bicyclo[2.2.1]hept-2-yloxy)-4-methoxyphenyl]-1,2,3,4-tetrahydro-2-pyrimidinone is prepared in 12.4% yield from the corresponding 1,2-dihydropyrimidinone:

MP=205°-208° C.

$^1$H NMR (300 MHz, DMSO): delta 8.2 (bs, 1H), 6.9–6.5 (m, 5H), 4.6 (m, 1H), 4.2 (bs, 2H), 3.8 (s, 3H), 2.5–1.0 (m, 10H).

EXAMPLE 70

5-[3-(Exo-Bicyclo[2.2.1]hept-2-yloxy)-4-Methoxyphenyl]hexahydro-2-Pyrimidinone (A) 3-[(3-bicyclo[2.2.1]hept-2-yloxy)-4-methoxyphenyl]glutaronitrile Cyanoacetic acid (18.1 g, 0.213 mmol) and exo-norbornyl isovanillin ether (17.5 g, 71.1 mmol) are dissolved in 80 ml of pyridine and 2 ml of piperidine and are heated to 100° C. for 40 hours. The reaction mixture is cooled to room temperature, poured into 200 ml of water and extracted with 2×100 ml ethyl acetate. The combined organics are washed with water, 1N HCl, saturated NaHCO$_3$ solution, water, dried over MgSO$_4$, filtered and concentrated in vacuo to provide a brown crystalline residue which is recrystallized from ether to afford 15.1 g (68.5%) of the dicyanide as a crystalline solid.

MP=122°-123° C.

$^1$H (300 MHz, CDCl$_3$): 6.82–6.65 (m, 3H), 4.14 (m, 1H), 3.8 (s, 3H), 3.3 (m, 1H), 2.77 (m, 1H), 2.45 (m, 1H), 2.3 (m, 1H), 1.8–1.0 (m, 8H).

(B) 3-[(3-bicyclo[2.2.1]hept-2-yloxy)-4-Methoxyphenyl]glutaramide

The above-prepared glutaronitrile from (A) (14.8 g, 47.7 mmol) is dissolved in 200 ml of acetone and is treated at 0° C. with 100 ml water, 33.8 ml 30% H$_2$O$_2$ and 21.2 ml 10% Na$_2$CO$_3$. The reaction is warmed slowly and stirred at room temperature for 14 hours. The reaction mixture is concentrated to 150 ml and the residue is partitioned between 100 ml of water and 200 ml of ethyl acetate. The organics are washed with water, dried over MgSO$_4$, filtered and concentrated in vacuo to provide the crude diamine which is titurated from ether to provide 13.8 g (84%) of the diamide as a crystalline solid.

MP=175°-177° C.

$^1$H NMR 300 MHz, CDCl$_3$): 6.8–6.6 (m, 3H), 4.15 (m, 1H), 3.75 (s, 3H), 3.6 (m, 1H), 2.6–1.0 (m, 14H).

(C) 5-[3-(exo-bicyclo[2.2.1]hept-2-yloxy)-4-methoxyphenyl]hexahydro-2-pyrimidinone The glutaramide (B) (1 g, 2.89 mmol) is dissolved in pyridine. To it is added lead tetraacetate (2.72 g, 6.13 mmol) and the mixture stirred for 20 hours at room temperature. The reaction mixture is diluted with water and extracted 2×100 ml ethyl acetate. The organics are washed with brine, dried over MgSO$_4$, filtered and concentrated in vacuo. The crude product is crystallized from ethyl acetate to provide 0.60 g (65.7%) of the cyclic urea as a crystalline solid.

MP=191°-192° C.

$^1$H NMR (300 MHz, CDCl$_3$): 6.8–6.6 (m, 3H), 5.35 (bs, 2H), 4.15 (m, 1H), 3.8 (s, 3H), 3.4 (m, 4H), 3.1 (m, 1H), 2.5–1.0 (m, 10H).

In like manner analogous formula (I) compounds wherein the bicycloalkyl group (R$^1$) is as defined below are prepared from appropriately substituted benzaldehydes:

R$^1$ endo-bicyclo[2.2.1]hept-2-yl
exo-bicyclo[3.2.1]oct-2-yl
endo-tricyclo[5.2.1.0$^{2,6}$]dec-4-yl
exo-tricyclo[5.2.1.0$^{2,6}$]dec-8-yl
exo-bicyclo[3.3.1.1$^{3,7}$]dec-2-yl
indan-2-yl

PREPARATION A

3-(Exo-Bicyclo[2.2.1]hept-2-yloxy)-4-Methoxybenzaldehyde

Endo-bicyclo[2.2.1]hept-2-ol (5.6 g, 5.0 mmol), isovanillin (7.6 g, 50.0 mmol) and triphenylphosphine (19.65 g, 75.0 mmol) are dissolved in 250 ml of dry tetrahydrofuran and to this mixture is added dropwise diethylazodicarboxylate (11.80 ml, 75.0 mmol). The reaction mixture is heated to reflux and is allowed to reflux for 48 hours. At this time the reaction mixture is cooled to room temperature and is diluted with 500 ml of diethyl ether. The collected organics are washed with 2×200 ml water, 2×200 ml 0.5N sodium hydroxide solution, 1×100 ml water and 1×100 ml saturated sodium chloride solution. The organics are dried over anhydrous sodium sulfate, filtered and concentrated in vacuo. The crude reaction mixture is chromatographed on SiO$_2$ (32–60 mesh) with 15% ethyl acetate/hexanes as the eluent. The appropriate fractions are collected and concentrated to yield 5.35 g (43.5%) of the exclusively exo-compound as a clear yellow oil.

$^1$H NMR (300 MHz, CDCl$_3$): delta 9.83 (s, 1H), 7.4 (dd, 1H, J=9 Hz, J=1 Hz), 7.3 (d, 1H, J=1 Hz), 6.95

(d, 1H, J=9 Hz), 4.28 (m, 1H), 3.91 (s, 3H), 2.6–1.0 (m, 10H).

Similarly, 3-(exo-Tricyclo[5.2.1.0$^{2,6}$]dec-4-yloxy)-4-methoxybenzaldehyde is prepared from tricyclo[5.2.1.0$^{2,6}$]decan-4-ol in 68.3% yield.

$^1$H NMR (300 MHz, CDCl$_3$): delta 9.8 (m, 1H), 7.4 (m, 2H), 6.95 (m, 1H), 4.95 (m, 1H), 4.0 (s, 3H), 2.8–1.2 (m, 14H).

3-(Endo-tricyclo[5.2.1.0$^{2,6}$]dec-8-yloxy)-4-methoxybenzaldehyde is prepared from tricyclo[5.2.1.0$^{2,6}$]decan-8-ol in 60.2% yield.

$^1$H NMR (300 MHz, CDCl$_3$): delta 9.8 (s, 1H), 7.4–7.3 (m, 2H), 6.85 (m, 1H), 4.8 (m, 1H), 3.85 (s, 3H), 2.3–0.9 (m, 14H).

PREPARATION B

2-(Bicyclo[2.2.1]hept-2-yl)-1,3-Benzodioxole

Norcamphor (25 g, 227 mmol) and pyrocatechol (22.7 g, 206 mmol) are dissolved in 500 ml of toluene and is heated to reflux in the presence of a catalytic amount of para-toluene sulfonic acid. The reaction mixture is refluxed over a soxhlet extractor charged with 3A molecular sieves overnight (15 hours). The reaction is cooled to room temperature and the toluene is removed in vacuo. The residue is dissolved in 500 ml ethyl ether and the ethereal layer is washed with 1×100 ml 2N NaOH, solution and 2×100 ml water and 1×100 ml saturated NaCl solution. The organics are dried over MgSO$_4$, filtered and concentrated in vacuo to yield 35.2 g (85%) of the catechol ketal as a white solid. MP: 42°–43° C.

$^1$H NMR (300 MHz, CDCl$_3$): delta 6.8 (m, 4H), 2.5–1.2 (m, 10H).

Following the above procedure tricyclo[5.2.1.0$^{2,6}$]decan-8-one is converted to 2-(tricyclo[5.2.1.0$^{2,6}$]dec-8-yl)-1,3-benzodioxole in 84.8% yield.

$^1$H NMR (300 MHz, CDCl$_3$): delta 6.9 (m, 4H), 2.7–1.0 (m, 14H);

benzobicyclo[2.2.1]heptan-2-one is converted to 2-(benzobicyclo[2.2.1]hept-2-yl)-1,3-benzodioxole in 93.5% yield.

$^1$H NMR (300 MHz, CDCl$_3$): delta 7.4–7.2 (m, 4H), 6.9–6.7 (m, 4H), 3.6 (m, 2H), 2.6 (m, 1H), 2.4 (m, 1H), 2.25 (m, 1H), 2.05 (m, 1H).

PREPARATION C

2-(Endo-Bicyclo[3.2.1]hept-2-yloxy)phenol

Aluminum chloride (4.9 g, 37 mmol) is suspended in 50 ml of dry ether and is cooled to 0° C. To this is added 12.5 ml of a 1M solution of lithium aluminum hydride in ether (12.5 mmol). The slurry is stirred for a half hour and to this is added the 2-(bicyclo[2.2.1]hept-2-yloxy)-1,3-benzodioxole (5.00 g, 25 mmol) as a solution in 50 ml ethyl ether. The solution is stirred for a half hour and then is carefully quenched dropwise with 50 ml of a saturated solution of sodium potassium tartrate. The resulting slurry is basified to a pH of with 2N NaOH solution and then is back titrated to pH with 10% hydrochloric acid solution. The layers are separated and the aqueous layer was re-extracted 2×150 ml ether. The combined organics are washed with 2×200 ml water and 1×200 ml saturated NaCl solution. The ethereals are dried over magnesium sulfate, filtered and concentrated in vacuo to yield (4.6 g 90%) of the phenol as a clear oil.

$^1$H NMR (300 MHz, CDCl$_3$): delta 7.0–6.7 (m, 4H), 6.7 (bs, 1H), 4.7 (m, 1H), 2.68 (m, 1H), 2.36 (m, 1H), 2.14 (m, 1H), 1.96 (m, 1H), 1.66 (m, 1H), 1.46 (m, 4H), 1.22 (m, 1H).

2-(Endo-tricyclo[5.2.1.0$^{2,6}$]dec-8-yloxy)phenol is prepared in 97% yield from 2-(tricyclo[5.2.1.0$^{2,6}$]dec-8-yl)-1,3-benzodioxole.

$^1$H NMR (300 MHz, CDCl$_3$): delta 7.0–6.7 (m, 4H), 5.7 (s, 1H), 4.65 (m, 1H), 2.6–1.0 (m, 14H).

2-(Endo-benzobicyclo[2.2.1]hept-2-yloxy)phenol is produced in 92.6% yield from 2-(benzobicyclo[2.2.1]hept-2-yl)-1,3-benzodioxole:

$^1$H NMR (300 MHz, CDCl$_3$): delta 7.35–7.2 (m, 4H), 6.8–7.0 (m, 4H), 5.25 (m, 1H), 4.95 (bs, 1H), 3.77 (m, 1H), 3.45 (m, 1H), 2.45 (m, 1H), 2.0 (m, 1H), 1.85 (1.2 (m, 1H).

PREPARATION D

4-Bromo-2-(Endo-Bicyclo[2.2.1]hept-2-yloxy)phenol 2-(Endo-bicyclo[2.2.1]hept-2-yloxy) (3.93 g, 19.3 mmol) is dissolved in 200 ml of chloroform and is cooled to −20° C. To this is added bromine (3.09 g, 19.3 mmol) as a 1M solution in chloroform dropwise over one-half hour. After addition is complete the solution is warmed to room temperature and concentrated in vacuo to yield 5.60 g (~100%) of the mono-bromo compound.

$^1$H NMR (300 MHz, CDCl$_3$): delta 7.0–6.7 (m, 3H), 5.65 (bs, 1H), 4.55 (m, 1H), 2.6 (m, 1H), 2.3 (m, 1H), 2.1 (m, 1H), 1.85 (m, 1H), 1.6 (m, 1H), 1.4 (m, 4H), 1.15 (m, 1H).

In like manner 2-(endo-tricyclo[5.2.1.0$^{2,6}$]dec-8-yloxy)phenol is converted to the corresponding 4-bromo derivative in 99% yield.

$^1$H NMR (300 MHz, CDCl$_3$): delta 7.0–6.7 (m, 3H), 5.75 (s, 1H), 4.65 (m, 1H), 2.7–1.0 (m, 14H).

2-(endo-benzobicyclo[2.2.1]hept-2-yloxy)phenol to the corresponding 4-bromo phenol in essentially quantitative yield:

$^1$H NMR (300 MHz, CDCl$_3$): delta 7.25–6.7 (m, 7H), 3.65 (m, 1H), 3.48 (m, 1H), 2.5–1.8 (m, 6H).

PREPARATION E

4-Bromo-2-(Endo-Bicyclo[2.2.1]hept-2-yloxy)-4-Methoxybenzene

The endo-bromophenol of Preparation D (5.60 g, 19.9 mmol) is dissolved in 50 ml of dry dimethylformamide and is treated with iodomethane (3.55 g, 25 mmol) and anhydrous potassium carbonate (3.46 g, 25 mmol) and is stirred at room temperature for 15 hours. The solution is poured into 600 ml of a 0.7 normal NaOH solution. The aqueous layer is extracted 2×300 ml ethyl ether and the combined organics are washed 4×100 ml water and 1×100 ml saturated NaCl solution. The organics are dried over magnesium sulfate, filtered and concentrated in vacuo to yield 5.14 g (87%) of methyl ether.

$^1$H NMR (300 MHz, CDCl$_3$): delta 6.9–6.6 (m, 3H), 4.55 (m, 1H), 3.82 (s, 3H), 2.6 (m, 1H), 2.3 (m, 1H), 2.05 (m, 2H), 1.6 (m, 1H), 1.42 (m, 4H), 1.16 (m, 1H).

In like manner, the following compounds are prepared from the appropriate bromophenols:

4-Bromo-2-(endo-tricyclo[5.2.1.0$^{2,6}$]dec-8-yloxy)-4-methoxybenzene:

$^1$H NMR (300 MHz, CDCl$_3$): delta 6.9 (m, 2H), 6.6 (m, 1H), 4.5 (m, 1H), 3.8 (s, 3H), 2.7–1.0 (m, 14H).

4-bromo-2-(endo-benzobicyclo[2.2.1]hept-2-yloxy)-4-methoxybenzene:

$^1$H NMR (300 MHz, CDCl$_3$): delta 7.2–6.9 (m, 6H), 6.6 (m, 1H), 5.0 (m, 1H), 3.65 (m, 1H), 3.50 (s, 3H), 3.35 (m, 1H), 2.4 (m, 1H), 1.85 (m, 1H), 1.75 (m, 1H), 1.2 (m, 1H).

PREPARATION F

Bicyclo[2.2.2]octan-2-ol

Bicyclo[2.2.2]-2-octene (20 g, 185 mmol) is dissolved in 100 ml of dry tetrahydrofuran and cooled to 0° C. To this is added borane-tetrahydrofuran complex (200 mmol) dropwise as a 1M solution in tetrahydrofuran. The reaction is warmed slowly to room temperature where it is stirred for 1 hour. The reaction is quenched slowly with 50 ml of 2N NaOH solution and 100 ml of 30% H$_2$O$_2$ and is warmed to 50° C. for 1 hour. The solution is diluted with 500 ml ethyl ether. The aqueous layer is saturated with NaCl and extracted with 100 ml ether. The organics are washed with 1×100 ml saturated sodium bisulfite solution, 1×100 ml water and 1×100 brine. The ethereal layer is dried with anhydrous Na$_2$SO$_4$, filtered and concentrated in vacuo to yield 19.27 g (83%) of the bicyclooctanol as a white solid. MP: 210°–212° C.

$^1$H NMR (90 MHz, CDCl$_3$): delta 3.93 (m, 1H), 2.5 (bs, 1H), 2.3–1.0 (m, ]2H).

PREPARATION G

Endo-Tricyclo[5.2.1.0$^{2.6}$]decan-2-ol

The tricyclodecanone (9.57 g, 63.8 mmol) is dissolved in 350 ml of dry tetrahydrofuran and is cooled to 0° C. The reaction mixture is treated with diisobutyl aluminum hydride as a solution in toluene (48 ml of a 1.5 molar solution, 7 mmol). The reaction is allowed, warmed slowly to room temperature and was stirred at room temperature for 14 hours. The reaction is then diluted with 500 ml of ethyl ether and is quenched with 20 ml of saturated NaK tartrate solution. The layers were separated and the aqueous is re-extracted with 100 ml ethyl ether. The combined organics are washed with 1×100 ml pH 7 phosphate buffer, 1×100 ml water, 1×100 ml brine, dried over MgSO$_4$, filtered and concentrated in vacuo to yield 9.3 g (95.8%) of the exclusively endo compound as a clear viscous oil.

$^1$H NMR (300 MHz, CDCl$_3$): delta 4.15 (m, 1H), 2.45 (m, 1H), 2.2–1.7 (m, 13H).

PREPARATION H 3-(Endo-Tricyclo[5.2.1.0$^{2.6}$]dec-8-yloxy) 4-Methoxybenzaldehyde The tricyclodecanol of Preparation G (5.17 g, 34.0 mmol), isovanillin (5.17 g, 34.0 mmol) triphenylphosphine (10.7 g, 40.8 mmol) and diethylazodicarboxylate (6.4 ml, 40.8 mmol) are dissolved in 200 ml of tetrahydrofuran and are refluxed together for 36 hours. The reaction is cooled to room temperature and diluted with 400 ml ether and 100 ml water. The layers are separated and dried over MgSO$_4$, filtered and concentrated in vacuo. The product is purified by flash chromatography (SiO$_2$ 10% ethyl acetate/hexanes) and the appropriate fractions are concentrated in vacuo to yield 1.28 g (14%) of the tricyclic-aryl aldehyde.

$^1$H NMR (300 MHz, CDCl$_3$): delta 9.8 (s, 1H), 7.43 (dd, 1H, J=9 Hz, J=1 Hz), 7.3 (d, 1H, J=1 Hz), 6.9 (d, 1H, J=9 Hz), 4.3 (m, 1H), 3.9 (s, 3H), 2.4–0.9 (m, 14H).

PREPARATION I 3-(Endo-Bicyclo[2.2.1]hept-2-yloxy)-4-Methoxybenzoic Acid

To a solution of 3-(endo-bicyclo[2.2.1]hept-2-yloxy)-4-methoxybenzaldehyde (2.46 g, 10 mmol) in 50 ml of acetone is added Jones reagent (6.5 ml of a 2.5 molar solution 16.9 mmol). The reaction is stirred at room temperature for 2 hours. The reaction mixture is diluted with 100 ml of water and extracted 2×50 ml ethyl acetate. The combined organics are washed with brine, water, dried over MgSO$_4$, filtered and concentrated in vacuo to yield the crude acid which is crystallized from ether to give 1.9 g (72.5%) of the acid as yellow crystals. MP=170°–171° C.

PREPARATION J

Methyl [3-(Endo-Bicyclo[2.2.1]hept-2-yloxy)-4-Methoxybenzoate

The 3-(Endo-bicyclo[2.2.1]hept-2-yloxy)-4-methoxybenzoic acid of Preparation I (1.9 g, 7.25 mmol) is dissolved in methanol, treated with concentrated sulfuric acid (1.1 ml, 10 mmol) and is refluxed for 3 hours. The reaction mixture is cooled to room temperature, concentrated in vacuo to 15 ml, diluted with 50 ml ethyl acetate and washed with water, aqueous NaHCO$_3$, water dried over MgSO$_4$ filtered and concentrated to in vacuo to yield 1.9 g (94.9%) of the ester as a thick yellow oil.

$^1$H NMR (60 MHz, CDCl$_3$): delta 10.0 (bs, 1H), 7.6–7.3 (m, 2H), 6.8–6.6 (m, 1H), 4.6 (m, 1H), 3.8 (s, 3H), 2.7–1.0 (m, 10H).

PREPARATION K 2-(Methylsulfinyl)-1-[3-(Endo-Bicyclo[2.2.1]hept-2-yloxy)-4-methoxyphenyl]Ethanone Pentane washed sodium hydride (50% in oil, 72 g, 15 mmol) is suspended in 10 ml of dry dimethylsulfoxide and is heated to 70° C. for 45 minutes. The reaction mixture is cooled to room temperature and diluted with 10 ml tetrahydrofuran. The reaction mixture is cooled to 0° C. and to it is added the ester of Preparation J (1.9 g, 6.9 mmol) dropwise over 20 minutes as a solution in tetrahydrofuran. The reaction mixture is stirred at 5° C. for one half hour and at room temperature for one half hour. The reaction mixture is poured onto 30 ml ice/water, acidified with 1N HCl and the product extracted 3×30 ml CH$_2$Cl$_2$. The combined organics are dried over MgSO$_4$, filtered and concentrated in vacuo to yield 1.5 g (67.5%) of the sulfoxide as a viscous yellow oil.

$^1$H NMR (60 MHz, CDCl$_3$): delta 7.6–7.2 (m, 2H), 7.0–6.7 (m, 1H), 4.6 (m, 1H), 4.35 (d, J=6 Hz), 3.9 (s, 3H), 2.75 (s, 3H), 2.7–1.0 (m, 10H).

PREPARATION L

2-Hydroxy-2-(Thiomethyl)-1-[3-(Endo-Bicyclo[2.2.1]hept-2-yloxy)-4-Methoxyphenyl]Ethanone The sulfoxide of Preparation K (1.5 g, 4.66 mmol) is dissolved in 15 ml of ethyl acetate and is treated with 15 ml of 1 normal HCl. The reaction is warmed to 50° C. for 16 hours. The cooled reaction mixture is quenched with 50 ml of water and extracted 2×50 ml ethyl acetate. The combined organics are washed 4×water, dried over MgSO$_4$, filtered and concentrated in vacuo to yield 1.48 g (98.6%) of the hydroxy sulfide as a thick oil.

¹H NMR (60 MHz, CDCl₃): delta 7.7–7.4 (m, 2H), 6.9–6.7 (m, 1H), 4.6 (m, 1H), 3.9 (s, 3H), 2.7–1.0 (m, 10H), 2.1 (s, 3H).

PREPARATION M 3-(bicyclo[2.2.1]hept,2-yloxy)-4-Methoxyphenylglyoxal

The hydroxy sulfide of Preparation L (1.48 g, 4.6 mmol) is dissolved in 10 ml of chloroform and is treated with Cu(OAc)₂.H₂O. The reaction mixture is stirred for 1.5 hours and is cooled, filtered through celite. The celite is washed with 3×chloroform. To the collected organics is added 20 ml of water and the mixture is basified with solid Na₂CO₃. The organics are separated, washed with water, dried over MgSO₄, filtered and concentrated in vacuo to yield 1.3 g (96.8%) of the alpha-keto aldehyde as a thick yellow oil.

¹H NMR (60 MHz, CDCl₃): delta 7.8–7.4 (m, 2H), 7.0–6.7 (m, 1H), 4.8 (m, 2H), 3.9 (s, 3H), 2.8–1.0 (m, 10H).

PREPARATION N 3-(Indan-2-yloxy)-4-Methoxybenzaldehyde

1-Indanol (5 g, 37 mmol), isovanillin (7.08 g, 46 mmol) triphenylphosphine (12.21 g, 46 mmol) and diethylazodecarboxylate (8.10 g, 46 mmol) are dissolved in 250 ml tetrahydrofuran and is refluxed until the indanol has completely disappeared by thin layer chromatography. The reaction is cooled and diluted with ml water and is extracted 3×50 ml ethyl ether. The collected organics are washed 2×50 ml water, 2×ml 1N NaOH solution, 2×50 ml water, 2×50 ml pH 7.3 molar phosphate buffer and 2×50 ml brine. The organic layer is dried over MgSO₄ filtered, concentrated in vacuo and flashed on SiO (32–60 mesh 4:1 1:1 hexanes/ethyl acetate) to give 2.29 g (23.1%) of the indanyl ether as a white solid.

¹H NMR (300 MHz, CDCl₃): delta 9.7 (s, 1H), 7.2 (m, 2H), 7.0–6.9 (m, 4H), 6.73 (m, 1H), 5.05 (m, 1H), 3.7 (s, 1H), 3.25 (dd, 2H, J=13 Hz, J=7 Hz), 3.15 (dd, 2H, J=13 Hz, J=3 Hz).

PREPARATION O 3-(Exo-Benzobicyclo[2.2.1]hept-2-yloxy)-4-methoxybenzaldehyde

The benzonorbornylformate (4 g, 0.022 mole) is dissolved in 50 ml of toluene and is treated with isovanillin (5.19 g, 0.034 mole) and a catalytic portion of p-toluenesulfonic acid. The reaction mixture is refluxed for 15 hours, cooled and diluted with 100 ml of ether. The organics are washed with 1N NaOH solution, water, brine, dried over MgSO₄, filtered and concentrated in vacuo. The crude material is purified by flash chromatography [SiO₂ 10→50% EtOAc/Hexane] to afford 0.78 g (11.4%) of the aldehyde as a yellow oil.

¹H NMR (300 MHz, CDCl₃): delta 9.7 (s, 1H), 7.4–6.9 (m, 7H), 4.4 (m, 1H), 3.9 (s, 3H), 3.6 (bs, 1H), 3.4 (bs, 1H), 2.25 (m, 1H), 1.95 (m, 3H).

PREPARATION P 3-(Exo-Bicyclo[2.2.1]hept-2-yloxy)-4-Methoxybenzyl Alcohol (3-Exo-bicyclo[2.2.1]hept-2-yloxy)-4-methoxybenzaldehyde (3.6 g, 14.6 mmol) is dissolved in 50 ml of methanol and to it is added portionwise sodium borohydride (0.18 g, 4.9 mmol). The reaction is stirred at 25° C. for 45 minutes. The reaction is quenched with 2 ml of water and is concentrated to 25 ml and is partitioned between 50 ml ethyl acetate and 50 ml water. The organic layer is separated, washed with brine, dried over MgSO₄, filtered and concentrated in vacuo to yield 3.37 g (93.1%) of the alcohol as a viscous oil.

¹H NMR (60 MHz, CDCl₃): delta 6.8 (m, 3H), 4.6 (bs, 2H), 4.2 (m, 1H), 3.8 (s, 3H), 2.8–1.0 (m, 10H).

Similarly, the following compounds are prepared from appropriate reactants:

3-(bicyclo[2.2.1]hept-2-yloxy)-4-methoxybenzyl alcohol is prepared in 94.7% yield as a 7:3 endo/exo mixture of isomers from an isomeric mixture of 3-(bicyclo[2.2.1-]hept-2-yloxy)-4-methoxybenzaldehydes.

¹H NMR (60 MHz, CDCl₃): delta 6.9 (m, 3H), 4.7 (m, 7H), 4.6 (bs, 2H), 4.2 (m, 3H), 3.9 (bs, 3H), 2.6 (bs, 3H), 2.6–1.0 (m, 10H);

3-(indan-2-yloxy)-4-methoxybenzyl alcohol in 91% yield:

¹H NMR (300 MHz, CDCl₃): delta 7.2 (m, 4H), 7.0–6.8 (m, 3H), 5.2 (m, 1H), 4.6 (s, 1H), 3.8 (s, 3H), 3.4 (m, 1H), 3.3 (m, 2H);

3-(endo-bicyclo[2.2.1]hept-2-yloxy)-4-methoxybenzyl alcohol in 98% yield:

¹H NMR (300 MHz, CDCl₃): delta 6.8 (m, 3H), 4.5 (m, 1H), 4.45 (bs, 1H), 3.75 (s, 3H), 2.8 (m, 1H), 2.6 (m, 1H), 2.2–1.0 (m, 8H).

PREPARATION Q 3-(Exo-Bicyclo[2.2.1]hept-2-yloxy)-4-Methoxybenzyl Bromide

The alcohol of Preparation P (3.3 g, 13.3 mmol) and carbon tetrabromide (8.83 g, 26.6 mmol) are dissolved in 50 ml of ether and is treated with triphenylphosphine (5.23 g, 19.95 mmol). The reaction is stirred for 2 hours at room temperature. The triphenylphosphine oxide was filtered off and is concentrated in vacuo. The residue is titrated with ethyl acetate. The resulting solid is further purified by flash chromatography with 75% hexanes/ethyl acetate as the eluent. The appropriate fractions are collected and concentrated in vacuo to yield 3.05 g (73.7%) of the bromide as thick yellow oil.

¹H NMR (60 MHz, CDCl₃): delta 6.8 (m, 3H), 5.4 (bs, 2H), 4.2 (m, 1H), 3.8 (s, 3H)), 2.6–1.0 (m, 10H).

An approximately 7:3 mixture of endo/exo isomers of 3-(bicyclo[2.2.1]hept-2-yloxy)-4-methoxybenzylbromides is similarly produced from the corrresponding carbinols.

¹H NMR (60 MHz, CDCl₃): delta 6.8 (m, 3H), 4.7 (m, 7H), 4.6 (bs, 2H), 4.2 (m, 3H), 3.85 (bs, 3H), 2.6–1.0 (m, 10H).

PREPARATION R 3-(Exo-Bicyclo[2.2.1]hept-2-yloxy)-4-Methoxybenzyl Cyanide

Sodium cyanide (804 mg, 16.4 mmol) is suspended in 30 ml DMSO and warmed to 70° C. A solution of the bromide of Preparation Q (3 g, 9.65 mmol) in 5 ml DMSO is added to the NaCN/DMSO suspension. The reaction is stirred at this temperature for 1 hour. The reaction mixture is cooled and quenched with 50 ml of water and extracted 3×50 ml ether. The combined organics are washed 3×water, dried over MgSO₄, filtered and concentrated in vacuo to yield a brown residue which is chromatographed on SiO₂ with 75% hexane/ethyl acetate as the eluent. Concentration in vacuo of the appropriate fractions yielded 1.2 g (48%) of the nitrile as a thick yellow oil.

$^1$H NMR (60 MHz, CDCl$_3$): delta 6.9 (m, 3H), 4.25 (m, 1H), 3.85 (s, 2H), 3.7 (s, 2H), 2.65–1.0 (m, 10H).

In like manner an approximately 7:3 endo/exo isomeric mixture of 3-(bicyclo[2.2.1]hept-2-yloxy)-4-methoxybenzyl cyanides is produced from the precursor benzyl bromides.

$^1$H NMR (300 MHz, CDCl$_3$): delta 6.9–6.7 (m, 3H), 4.65 (m, 7H), 4.25 (m, 3H), 3.85 (bs, 3H), 3.7 (bs, 2H), 2.65–1.1 (m, 10H).

PREPARATION S

3-(Exo-Tricyclo[5.3.1.1$^{3,7}$]dec-2-yloxy)-4-Methoxyphenylbenzaldehyde

Isovanillin (10.75 g, 70.72 mmol), 2-adamantanol (8.6 g, 56.5 mmol), triphenylphosphine (18.53 g, 70.72 mmol) and diethylazodicarboxylate (11.12 ml, 70.72 mmol) are dissolved in 280 ml tetrahydrofuran and are warmed to reflux for 24 hours. The reaction is cooled and diluted with 500 ml of ether and is washed with 2×100 ml water, 2×100 ml 0.5N NaOH solution, 2×100 ml water, 1×100 ml 3 molar pH 7 phosphate buffer, 1×100 ml brine. The organics are concentrated in vacuo to 100 ml and diluted with 500 ml hexanes to precipitate triphenylphosphine oxide. The solution is dried over MgSO$_4$, filtered and concentrated in vacuo. The pure aldehyde is isolated by a standard bisulfite formation/liberation procedure to yield 5.29 g (33%) of the aldehyde as a viscous oil.

$^1$H NMR (300 MHz, CDCl$_3$): delta 7.4 (m, 2H), 6.95 (m, 1H), 4.52 (bs, 1H), 3.92 (s, 3H), 2.3–1.4 (m, 14H).

PREPARATION T

3-Exo-Tricyclo[5.2.1.0$^{2,6}$]dec-8-yloxy-4-Methoxybenzaldehyde

Endo-Tricyclo[5.2.1.0$^{2,6}$]decan-8-ol (5.17 g, 34.0 mmol), isovanillin (5.17 g, 34.0 mmol) triphenylphosphine (10.7 g, 40.8 mmol) and diethylazodicarboxylate (6.4 ml, 40.8 mmol) are dissolved in 200 ml of tetrahydrofuran and are refluxed together for 36 hours. The reaction is cooled to room temperature and diluted with 400 ml ether and 100 ml water. The layers are separated and the organics are washed with 2×100 ml H$_2$O, 2×0.5 normal NaOH, 2×100 ml H$_2$O, 1×100 ml brine, dried over MgSO$_4$, filtered and concentrated in vacuo. The product is purified by flash chromatography (SiO$_2$ 10% ethyl acetate/hexanes) and the appropriate fractions are concentrated in vacuo to yield 1.28 g (14%) of the tricycli-aryl aldehyde.

$^1$H NMR (300 MHz, CDCl$_3$): delta 9.8 (s, 1H), 7.43 (dd, 1H, J=9 Hz, J=1 Hz), 7.3 (d, 1H, J=1 Hz), 6.9 (d, 1H, J=9 Hz), 4.3 (m, 1H), 3.9 (s, 3H), 2.4–0.9 (m, 14H).

PREPARATION U

1-[3-(Bicyclo[2.2.1]hept-2-yl)-4-Methoxyphenyl)ethan-1-O1

The aldehyde (3 g, 12.2 mmol) is dissolved in 10 ml dry THF and is added to a solution of methylmagnesium bromide (15 mmol) in 10 ml of THF. The reaction mixture is allowed to warm slowly to room temperature and is stirred at room temperature overnight. The reaction is quenched with 10 ml aqueous NH$_4$Cl and the product is extracted 2×ethyl acetate. The combined organics are washed with brine dried over MgSO$_4$, filtered and concentrated in vacuo to yield 2.9 g (90.7%) of the carbinol as a 7.3 endo/exo mixture of isomers.

$^1$H NMR (60 MHz, CDCl$_3$): delta 7.8–6.8 (m, 3H), 5.0–4.0 (m, 2H), 4.0 (2s, 3H), 3.0–1.2 (m, 13H).

1-[3-(indan-2-yloxy)-4-methoxyphenyl]ethan-1-ol is prepared in like manner from 3-indan-2-yloxy-4-methoxybenzaldehyde in 97.5% yield.

$^1$H NMR (60 MHz CDCl$_3$): delta 7.2–6.7 (m, 7H), 5.1 (m, 1H), 4.9 (q, 1H, J=6 Hz), 3.8 (s, 3H), 3.3 (m, 4H), 1.5 (d, 3H, J=6 Hz).

PREPARATION V

Tricyclo[3.2.1.0$^{2,6}$]decan-4-ol

Tricyclo[5.2.1.0$^{2,6}$]decan-4-one (1.5 g, 10 mmol) is dissolved in 25 ml of absolute ethanol and treated with sodium borohydride (0.189 g, 5.0 mmol). The reaction is stirred 24 hours, concentrated in vacuo and the resulting crude is redissolved in ether. The organics are washed 2×H$_2$O, 2×brine, dried, filtered and concentrated in vacuo to afford 1.47 g (96.79%) of the alcohol as a clear oil.

$^1$H NMR (300 MHz, CDCl$_3$): delta 4.2 (m, 1H), 2.4–1.2 (m, 14H).

$^{13}$C NMR (75.43 MHz, CDCl$_3$): delta 76.71, 43.10, 41.75, 39.48, 34.43, 22.32 (6 lines).

PREPARATION W

1-[3-[Bicyclo[2.2.1]hept-2-yloxy)-4-Methoxyphenyl]ethanone

The title carbinol of Preparation U (2.9 g, 11.07 mmol) is dissolved in 20 ml of acetone and treated with 12.5 ml of 1 Molar Jones reagent. The reaction is stirred for 2 hours, quenched with water and the product is extracted 3×ethyl acetate. The combined organics are washed with H$_2$O, brine, dried over MgSO$_4$, filtered and concentrated in vacuo. The crude product is chromatographed on SiO$_2$ with 4:1 hexane/ethyl acetate as the eleuent to yield 1.5 g (52.7%) of the methyl ketone as a viscous oil as a mixture of isomers.

$^1$H NMR (60 MHz, CDCl$_3$): delta 7.7–7.3 (m, 2H), 7.2–6.8 (m, 1H), 5.0–4.1 (m, 1H), 4.0 (bs, 3H), 3.0–1.0 (m, 10H), 2.6 (s, 3H).

1-[3-(Indan-2-yloxy)-4-methoxyphenyl]ethanone is prepared in a similar manner from 1-[3-(indan-2-yloxy)-4-methoxyphenyl]ethan-1-ol in 52.1% yield.

$^1$H NMR (60 MHz, CDCl$_3$): delta 7.6–6.7 (m, 7H), 5.2 (m, 1H), 3.9 (s, 3H), 3.3 (m, 4H), 2.4 (s, 3H).

PREPARATION X

3-(Endo-Bicyclo[2.2.1]hept-2-yloxy)-4-Methoxybenzyl Chloride

A solution of 3-(endo-bicyclo[2.2.1]hept-2yloxy)-4-methoxybenzyl alcohol (8.5 g, 34.3 mmol) and triethylamine (5.7 ml, 41.2 mmol) in methylene chloride (75 ml) is cooled to 0° C. and to it is added methanesulfonyl chloride (2.9 ml, 37.8 mmol) dropwise. The reaction is then stirred for 2 hours and is worked up by dilution with water and removal of the methylene chloride phase. The aqueous layer is re-extracted with methylene chloride, the combined methylene chloride extracts washed with water and brine, then dried over Na$_2$SO$_4$, filtered and concentrated in vacuo to afford 8.0 g (87.5%) of the benzyl chloride as an orange oil.

$^1$H NMR (300 MHz, CDCl$_3$): delta 6.8 (m, 3H), 4.5 (m, 1H), 4.35 (s, 1H), 3.8 (s, 3H), 2.6–1.0 (m, 10H).

In like manner, 3-(indan-2-yloxy)-4-methoxybenzyl-chloride is obtained from the corresponding benzyl alcohol.

HRMS 288.0900 (M+) Calcd. for $C_{17}H_{17}O_2Cl$, 288.0913.

PREPARATION Y

3-(Indan-2-yloxy)-4-(Methoxybenzyl Cyanide 3-(Indan-2-yloxy)-4-methoxybenzyl chloride (17.7 g, 61.4 mmol) is dissolved in 150 ml dimethylsulfoxide and is treated with potassium cyanide (7.9 g, 121.5 mmol). The reaction is stirred at room temperature for 4.5 hours then partitioned between water and ethyl acetate. It is washed 2×H₂O, 2×brine, dried over MgSO₄, filtered and concentrated in vacuo. The crude material is purified by flash chromatography (SiO₂, 3:1 hexane/ethyl acetate). The appropriate fractions are combined and concentrated in vacuo to afford 9.2 g (53%) of the benzyl cyanide as a pale yellow solid.

$^1$H NMR (CDCl₃, 300 MHz): delta 7.3–7.2 (m, 4H), 6.9 (m, 3H), 5.22 (m, 1H), 3.9 (s, 1H), 3.75 (s, 2H), 3.5–3.2 (m, 4H).

Similarly, 3-(endo bicyclo[2.2.1]hept-2-yloxy)-4-methoxybenzyl cyanide is prepared in 52% yield from the corresponding benzyl chloride.

$^1$H NMR (300 MHz, CDCl₃): delta 6.8 (m, 3H), 4.5 (m, 1H), 3.8 (s, 3H), 3.6 (s, 2H), 2.5–1.0 (m, 10H).

PREPARATION Z

3-(Bicyclo[2.2.1]hept-2-yloxy)-4-Methoxybenzaldehyde (7:3 Endo:Exo Mixture)

Isovanillin (50 g, 0.328 mol) is placed in a 1 liter round bottom flask which is equipped with a stir bar and reflux condensor and is charged with 500 ml of dimethylformamide. Potassium carbonate (45.3 g, 0.328 mol) is added to the reaction mixture which is heated to 80° C. At this temperature exo-2-bromonorbornane (12.57 g, 0.072 mol, 0.219 equivalents) is added and the reaction mixture is heated to 120° C. for 48 hours. The reaction is then cooled to room temperature and poured into 300 ml of water. The aqueous layer is extracted with ethyl ether (3×100 ml). The ethereal layer is washed with 1N sodium hydroxide solution (4×100 ml), water (3×100 ml) and saturated sodium chloride solution (3×100 ml). The organic layer is dried over anhydrous magnesium sulfate, filtered and concentrated in vacuo to yield 15.47 g of a green/brown oil. The crude product is purified by flash chromatography using a gradient eluent system of ethyl acetate/hexane [10% ethyl acetate/hexane→20% ethyl acetate/hexane] to yield 7.76 g (14.4%) of the aldehyde as a white solid. MP: 75.5° C.–79.5° C.

The material represents a 7:3 mixture of endo:exo bicyclo[2.2.1]hept-2-yl ethers.

$^1$H-nmr (300 MHz CDCl₃): delta 9.82 (s, 1H), 7.41 (m, 1H), 7.31 (d, 1H), 6.95 (d, 1H, J=9 Hz), 4.6–4.7 (m, 7H) [endo], 4.2–4.3 (m, 0.3H) (exo), 3.93 (s, 2.1H) [endo], 3.91 (s, 0.9H) [exo], 2.7–0.9 (m, 10H).

The following compounds are prepared in like manner from appropriate reactants:

3-(exo-tricyclo[5.2.1.0$^{2.6}$]dec-4-yloxy)-4-methoxybenzladehyde in 60.2% yield:

$^1$H NMR (300 MHz, CDCl₃): delta 9.8 (s, 1H), 7.4–7.3 (m, 2H), 6.85 (m, 1H), 4.8 (m, 1H), 3.85 (s, 3H), 2.3–3.9 (m, 14H).

PREPARATION AA

3-(Endo-Bicyclo[2.2.1]hept-2-yloxy)-4-Methoxybenzaldehyde

4-Bromo-2-(endo-bicyclo[2.2.1]hept-2-yloxy)-4-methoxybenzene (5.14 g, 17.4 mmol) is dissolved in 150 ml of dry tetrahydrofuran. This solution is cooled to −78° C. and to it is added dropwise 20.5 ml of a 1.7M solution of tert-butyllithium (34.8 mmol) as a solution in pentane. The solution is stirred at −78° C. for 1.5 hours and is then treated with N,N-dimethylformamide (13.2 ml, 170 mmol) as a solution in 30 ml of tetrahydrofuran. The reaction is stirred at −78° C. for one half hour and is warmed slowly to room temperature. The reaction mixture is diluted with 300 ml ethyl ether and washed with 3×200 ml H₂O and 1×100 ml brine. The organics are dried over anhydrous magnesium sulfate, filtered and concentrated in vacuo to yield 4.04 g (95%) of the benzaldehyde as a white powder. MP 87°–88° C.

$^1$H NMR (300 MHz, CDCl₃): delta 9.82 (s, 1H), 7.4 (dd, 1H, J=9, J=1), 7.3 (d, 1H, J=1 Hz), 6.9 (d, J=9 Hz), 4.65 (m, 1H), 3.93 (s, 1H), 2.65 (m, 1H), 2.3 (m, 1H), 2.15 (m, 1H), 2.05 (m, 1H), 1.6 (m, 1H), 1.4 (m, 4H), 1.08 (m, 1H).

Following the above procedure, the following benzaldehyde derivative is produced from the corresponding bromo reactant: 3-(endo-tricyclo[5.2.1.0$^{2.6}$]dec-8-yloxy)-4-methoxybenzaldehyde in 64% yield.

$^1$H NMR (300 MHz, CDCl₃): delta 9.8 (s, 1H), 7.5–7.3 (m, 2H), 6.95 (m, 1H), 4.7 (m, 1H), 3.97 (s, 3H), 2.8–1.0 (m, 14H).

3-(endo-benzobicyclo[2.2.1]hept-2-yloxy)-4-methoxybenzaldehyde in 51.8% yield:

$^1$H NMR (300 MHz, CDCl₃): delta 9.6 (s, 1H), 7.3–7.2 (m, 2H), 7.1–6.9 (m, 4H), 6.7 (m, 1H), 5.0 (m, 1H), 3.6 (m, 1H), 3.55 (s, 3H), 3.25 (m, 1H), 2.2 (m, 1H), 1.8 (m, 1H), 1.65 (m, 1H), 1.05 (m, 1H).

PREPARATION BB

3-(Exo-Bicyclo[2.2.2]oct-2-yloxy)-4-Methoxybenzaldehyde

Bicyclo[2.2.2]-2-octanol (5.00 g, 40 mmol), isovanillin (6.09 g, 40 mmol) and triphenylphosphine (13.1 g, 50 mmol) are dissolved in dry tetrahydrofuran. To this reaction mixture is added dropwise diethylazodicarboxylate (8.71 g, 50 mmol). The reaction is stirred for 1 hour at room temperature and is refluxed for 80 hours. The reaction mixture was cooled and concentrated in vacuo and the residue is mashed 3×150 ml of ether to remove the desired material from the triphenylphosphine oxide. The combined ethereal layers are washed with 2×100 ml H₂O, 2×100 ml 2N NaOH solution, 2×100 ml H₂O and 2×100 ml brine. The organics are dried, filtered and concentrated in vacuo. The compound is purified by flash silica gel (32–80 mesh) chromatography with 20% ethyl acetate/hexane. The appropriate fractions are concentrated in vacuo to yield 3.32 g (32%) of product as a viscous oil.

$^1$H NMR (250 MHz, CDCl₃): delta 7.4 (dd, 1H, J=8.5 Hz, J=10.5 Hz), 7.35 (d, 1H, J=10.5 Hz), 6.95 (d, 1H, J=8.5 Hz), 4.52 (m, 1H), 3.91 (s, 3H), 2.2–1.3 (m, 12H).

$^{13}$C NMR (63 MHz, CDCl₃): delta 190.9, 155.7, 147.9, 129.97, 126.2, 112.6, 110.9, 77.5, 56.1, 34.74, 28.18, 25.25, 24.55, 23.29, 22.78, 19.09 (16 lines).

PREPARATION CC

3-(Exo-Bicyclo[3.2.1]oct-2-yloxy)-4-Methoxybenzaldehyde

The cis-bicyclo[3.2.1]-3-octanol (1.90 g, 0.015 mol) triphenylphosphine (4.72 g, 0.018 mol), isovanillin (2.73 g, 0.018 mol) and diethylazodicarboxylate (2.83 ml, 0,018 mol) are dissolved in 75 ml of dry tetrahydrofuran. The reaction is refluxed for 15 hours, cooled and diluted with 50 ml ethyl ether and 50 ml water. The aqueous layer is separated and extracted with 2×25 ml ether. The combined organics are washed with 2×25 ml water, 2×25 ml 1N NaOH solution, 2×25 ml water, 2×25 ml 3M pH 7 phosphate buffer and 2×25 ml brine. The organics are dried over MgSO4 and concentrated in vacuo to 50 ml which is diluted with 250 ml of hexanes and filtered to remove precipitated triphenylphosphine oxide. This is repeated 3 times to remove the remainder of the triphenylphosphine oxide. The resulting organic layer is dried over MgSO4 filtered and concentrated in vacuo to yield 1.68 g (43%) of the aryl ether as a clear oil.

$^1$H NMR (300 MHz, CDCl$_3$): delta 10.01 (s, 1H), 7.3–7.1 (m, 2H), 6.8 (m, 1H), 4.4 (m, 1H), 3.78 (s, 3H), 2.3–1.3 (m, 12H).

PREPARATION DD

3-(Endo-Tricyclo[5.3.1.1$^{3,7}$]dec-2-yloxy)-4-Methoxyphenylbenzaldehyde

Isovanillin (10.75 g, 70.72 mmol), 2-adamantanol (8.6 g, 56.5 mmol), triphenylphosphine (18.53 g, 70.72 mmol) and diethylazodicarboxylate (11.12 ml, 70.72 mmol) are dissolved in 280 ml tetrahydrofuran and are warmed to reflux for 24 hours. The reaction is cooled and diluted with 500 ml of ether and is washed with 2×100 ml water, 2×100 ml 0.5N NaOH solution, 2×100 ml water, 1×100 ml 3 molar pH 7 phosphate buffer, 1×100 ml brine. The organics are concentrated in vacuo to 100 ml and diluted with 500 ml hexanes to precipitate triphenylphosphine oxide. The solution is dried over MgSO$_4$, filtered and concentrated in vacuo. The pure aldehyde is isolated by a standard bisulfite formation/liberation procedure to yield 5.29 g (33%) of the aldehyde as a viscous oil.

$^1$H NMR (300 MHz, CDCl$_3$): delta 7.4 (m, 2H), 6.95 (m, 1H), 4.52 (bs, 1H), 3.92 (s, 3H), 2.3–1.4 (m, 14H).

We claim:

1. A compound having the formula

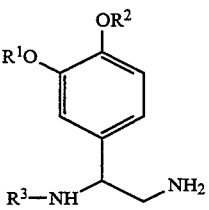

(V)

wherein R$^1$ is selected from the group consisting of bicyclo[2.2.1]heptyl, bicyclo[2.2.2]octyl, bicyclo[3.2.1]octyl, tricyclo[5.2.1.0$^{2,6}$]decyl, tricyclo [3.3.1.1$^{3,7}$]decyl and indanyl;

R$^2$ is methyl or ethyl; and

R$^3$ is hydrogen, (C$_{1-5}$) alkyl, (C$_{2-5}$)alkenyl, benzyl or phenethyl.

2. A compound having the formula

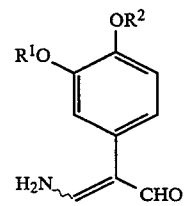

(XII)

wherein R$^1$ is selected from the group consisting of bicyclo[2.2.1]heptyl, bicyclo[2.2.2]octyl, bicyclo[3.2.1]octyl, tricyclo[5.2.1.0$^{2,6}$]decyl, tricyclo [3.3.1.1$^{3,7}$]decyl and indanyl; and R$^2$ is methyl or ethyl.

3. A compound having the formula

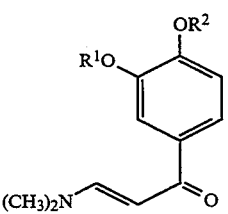

(XVI)

wherein R$^1$ is selected from the group consisting of bicyclo[2.2.1]heptyl, bicyclo[2.2.2]octyl, bicyclo[3.2.1]octyl, tricyclo[5.2.1.0$^{2,6}$]decyl, tricyclo [3.3.1.1$^{3,7}$]decyl and indanyl; and R$^2$ is methyl or ethyl.

* * * * *